US012319697B2

United States Patent
Willot et al.

(10) Patent No.: US 12,319,697 B2

(45) Date of Patent: Jun. 3, 2025

(54) PROCESS FOR PREPARING IMIDAZOLE DERIVATIVES

(71) Applicant: Bayer Aktiengesellschaft, Leverkusen (DE)

(72) Inventors: Matthieu Willot, Duesseldorf (DE); Ruediger Fischer, Pulheim (DE); Dominik Hager, Monheim (DE); Laura Hoffmeister, Duesseldorf (DE); Marc Mosrin, Monheim am Rhein (DE); David Wilcke, Duesseldorf (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 1073 days.

(21) Appl. No.: 17/283,661

(22) PCT Filed: Oct. 9, 2019

(86) PCT No.: PCT/EP2019/077304

§ 371 (c)(1),
(2) Date: Apr. 8, 2021

(87) PCT Pub. No.: WO2020/074558

PCT Pub. Date: Apr. 16, 2020

(65) Prior Publication Data

US 2022/0009930 A1 Jan. 13, 2022

(30) Foreign Application Priority Data

Oct. 11, 2018 (EP) .................................... 18199885

(51) Int. Cl.

| | |
|---|---|
| ***C07D 487/04*** | (2006.01) |
| ***B01J 31/24*** | (2006.01) |
| ***C07D 471/04*** | (2006.01) |

(52) U.S. Cl.

CPC ........ *C07D 487/04* (2013.01); *B01J 31/2404* (2013.01); *C07D 471/04* (2013.01); *B01J 2531/824* (2013.01)

(58) Field of Classification Search

CPC ............................ C07D 487/04; C07D 471/04

See application file for complete search history.

(56) References Cited

U.S. PATENT DOCUMENTS

| | | | |
|---|---|---|---|
| 10,875,858 | B2 | 12/2020 | Mosrin et al. |
| 2020/0045976 | A1 | 2/2020 | Wilcke et al. |
| 2020/0054017 | A1 | 2/2020 | Wilcke et al. |

FOREIGN PATENT DOCUMENTS

| | | | |
|---|---|---|---|
| WO | 2007/042544 | A2 | 4/2007 |
| WO | 2018/033448 | A1 | 2/2018 |
| WO | 2018/130437 | A1 | 7/2018 |
| WO | 2018/130443 | A1 | 7/2018 |

OTHER PUBLICATIONS

PCT International Search Report for PCT/EP2019/077304, mailed Oct. 31, 2019.

Mosrin, et al., "TMPZnCl—LiCl: A New Active Selective Base for the Directed Zincation of Sensitive Aromatics and Heteroaromatics," Org. Lett., (2009), vol. 11, No. 8: 1837-1840.

Stathakis, et al., "TMPZnOPiv-LiCl: A New Base for the Preparation of Air-Stable Solid Zinc Pivalates of Sensitive Aromatics and Heteroaromatics," Org. Lett., (2013), vol. 15, No. 6: 1302-1305.

Hlavinka, et al., "Zn(tmp)2: A Versatile Base for the Selective Functionalization of C—H Bonds," Organometallics, (2007), vol. 26, No. 17: 4105-4108.

Kumar, et al., "Benzimidazole-based optical probe for selective detection of multiple-cations via dual-channel analysis," Tetrahedron Letters, (2012), vol. 53: 5691-5694.

*Primary Examiner* — Alicia L Otton

(74) *Attorney, Agent, or Firm* — Michael VanEngelen

(57) ABSTRACT

The present invention relates to a process for preparing imidazole derivatives of the formula (II) proceeding from compounds of the structure Q-H via intermediates of the formula (IIIa) or (IIIb)

(II)

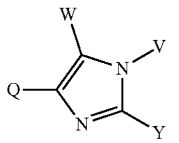

(IIIa)

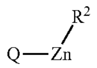

(IIIb)

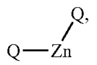

in which

Q represents a structural element

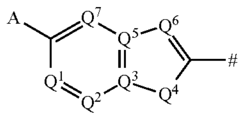

where the symbol # represents the bond to the remainder of the molecule and A, $Q^1$, $Q^2$, $Q^3$, $Q^4$, $Q^5$, $Q^6$ and $Q^7$, and also $R^2$, W, V and Y have the meanings given in the description.

12 Claims, No Drawings

PROCESS FOR PREPARING IMIDAZOLE DERIVATIVES

CROSS-REFERENCE TO RELATED APPLICATIONS

This application is the National Stage entry of International Application No. PCT/EP2019/077304, filed 9 Oct. 2019, which claims priority to European Patent Application No. 18199885.7, filed 11 Oct. 2018.

BACKGROUND

Field

The present invention relates to a process for preparing imidazole derivatives of the formula (II)

(II)

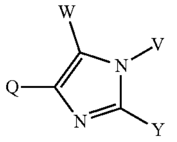

proceeding from compounds Q-H via intermediates of the formula (IIIa) or (IIIb)

(IIIa)

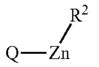

(IIIb)

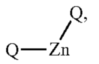

in which the structural elements shown in the formulae (II), (IIIa) and (IIIb) have the definitions given below. The invention further relates to imidazole derivatives and intermediates of this kind.

Imidazole derivatives of the formula (II) are of great industrial significance for the pharmaceutical and agrochemical industry and are an important intermediate, inter alia, in the preparation of compounds that are effective as pesticides, for example.

DESCRIPTION OF RELATED ART

The literature discloses that compounds of the formula (II) can be prepared, for example, in a first step by condensation of imidazole-4-carboxylic acid derivatives with ortho-substituted bis(amine), amine alcohol or amine thiol (hetero)aryl derivatives in the presence of an acid (cf. WO 2007/042544 or *Tetrahedron Letters* 2012, 53, 5691-5694). It is furthermore known from the literature that compounds of the formula (II) can be obtained in a cyclization reaction from imidazolecarboxylic acid derivatives with ortho-diamines or ortho-aminoalcohols and in a cyclization reaction of α-haloketones with aromatic amines (cf. WO 2018/130443 or WO 2018/130437). However, the chemical synthesis methods that have been described in the prior art to date for such imidazole derivatives very frequently make use of methods that are not economically implementable from an industrial point of view and/or have other disadvantages.

Disadvantages are low chemical yields, performance at very high temperatures (about 150° C. to 250° C.) and the possibility of difficult regio- and chemoselectivity of the condensation, in particular in the case of imidazopyridine and imidazopyridazine derivatives. The preparation is therefore very expensive and unsuitable for industrial scale commercial processes. Moreover, corresponding compounds are barely commercially available. This applies in particular to 5-alkylsulfanyl-1H-imidazole-4-carboxylic acid derivatives.

With regard to the disadvantages outlined above, there is an urgent need for a simplified, industrially and economically performable method for preparing imidazole derivatives, in particular imidazole derivatives of the formula (II). The imidazole derivatives obtainable by this process sought are preferably to be obtained with good yield, high purity and in an economic manner.

It is known from the literature that halogenated pyridine derivatives can be prepared using an organozinc base (cf. WO 2018/033448).

SUMMARY

It has been found that, surprisingly, imidazole derivatives of the formula (II) can be prepared advantageously in a process using an organozinc base.

The present invention accordingly provides a method for preparing compounds of the formula (II)

(II)

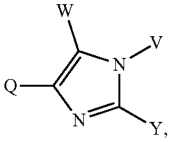

in which (Configuration 1)

Q represents a structural element

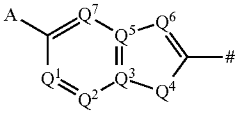

where the symbol # indicates the bond to the rest of the molecule and $Q^1$ represents N or $CR^6$,
$Q^2$ represents N or $CR^6$,
$Q^3$ represents N or C,
$Q^4$ represents O, S, N, $CR^6$ or $NR^7$,
$Q^5$ represents N or C,
$Q^6$ represents N or CH and
$Q^7$ represents N or CH, where at most five of the variables $Q^1$, $Q^2$, $Q^3$, $Q^4$, $Q^5$, $Q^6$ and $Q^7$ simultaneously represent nitrogen and $Q^3$ and $Q^1$ do not simultaneously represent N and $R^6$ represents hydrogen, $(C_1\text{-}C_4)$-alkyl, $(C_1\text{-}C_4)$-haloalkyl, $(C_1\text{-}C_4)$-cyanoalkyl, $(C_1\text{-}C_4)$-alkoxy-$(C_1\text{-}C_4)$-alkyl, $(C_1\text{-}C_4)$-haloalkoxy-$(C_1\text{-}C_4)$-alkyl, $(C_2\text{-}C_4)$-alkenyl, $(C_2\text{-}C_4)$-alkenyloxy-$(C_1\text{-}C_4)$-alkyl, $(C_2\text{-}C_4)$-haloalkenyloxy-$(C_1\text{-}C_4)$-alkyl, $(C_2\text{-}C_4)$-haloalkenyl, $(C_2\text{-}C_4)$-cyanoalkenyl, $(C_2\text{-}C_4)$-alkynyl, $(C_2\text{-}C_4)$-alkynyloxy-$(C_1\text{-}C_4)$-alkyl, $(C_2\text{-}C_4)$-haloalkynyl, $(C_3\text{-}C_6)$-cycloalkyl, $(C_3\text{-}C_6)$-cycloalkyl-$(C_3\text{-}C_6)$-cycloalkyl, $(C_1\text{-}C_4)$-alkyl-$(C_3\text{-}C_6)$-cycloalkyl, halo-$(C_3$-$C_6)$-cycloalkyl, $(C_1$-$C_4)$-alkylthio-$(C_1$-$C_4)$-alkyl, $(C_1$-$C_4)$-alkylsulfinyl-$(C_1$-$C_4)$-alkyl, $(C_1$-$C_4)$-alkylsulfonyl-$(C_1$-$C_4)$-alkyl or $(C_1$-$C_4)$-alkylcarbonyl-$(C_1$-$C_4)$-alkyl, $R^7$ represents $(C_1$-$C_4)$-alkyl, $(C_1$-$C_4)$-haloalkyl, $(C_1$-$C_4)$-cyanoalkyl, $(C_1$-$C_4)$-alkoxy-$(C_1$-$C_4)$-alkyl, $(C_1$-$C_4)$-haloalkoxy-$(C_1$-$C_4)$-alkyl, $(C_2$-$C_4)$-alkenyl, $(C_2$-$C_4)$-alkenyloxy-$(C_1$-$C_4)$-alkyl, $(C_2$-$C_4)$-haloalkenyloxy-$(C_1$-$C_4)$-alkyl, $(C_2$-$C_4)$-haloalkenyl, $(C_2$-$C_4)$-cyanoalkenyl, $(C_2$-$C_4)$-alkynyl, $(C_2$-$C_4)$-alkynyloxy-$(C_1$-$C_4)$-alkyl, $(C_2$-$C_4)$-haloalkynyl, $(C_3$-$C_6)$-cycloalkyl, $(C_3$-$C_6)$-cycloalkyl-$(C_3$-$C_6)$-cycloalkyl, $(C_1$-$C_4)$-alkyl-$(C_3$-$C_6)$-cycloalkyl, halo-$(C_3$-$C_6)$-cycloalkyl, $(C_1$-$C_4)$-alkylthio-$(C_1$-$C_4)$-alkyl, $(C_1$-$C_4)$-alkylsulfinyl-$(C_1$-$C_4)$-alkyl, $(C_1$-$C_4)$-alkylsulfonyl-$(C_1$-$C_4)$-alkyl or $(C_1$-$C_4)$-alkylcarbonyl-$(C_1$-$C_4)$-alkyl and A represents hydrogen, cyano, halogen, $(C_1$-$C_4)$-alkyl, $(C_1$-$C_4)$-haloalkyl, $(C_2$-$C_4)$-alkenyl, $(C_2$-$C_4)$-haloalkenyl, $(C_2$-$C_4)$-alkynyl, $(C_2$-$C_4)$-haloalkynyl, $(C_3$-$C_6)$-cycloalkyl, $(C_3$-$C_6)$-cycloalkyl-$(C_3$-$C_6)$-cycloalkyl, $(C_1$-$C_4)$-alkyl-$(C_3$-$C_6)$-cycloalkyl, $(C_1$-$C_4)$-alkoxy, $(C_1$-$C_4)$-haloalkoxy, $(C_1$-$C_4)$-alkoxyimino, $(C_1$-$C_4)$-alkylthio, $(C_1$-$C_4)$-haloalkylthio, $(C_1$-$C_4)$-alkylsulfinyl, $(C_1$-$C_4)$-haloalkylsulfinyl, $(C_1$-$C_4)$-alkylsulfonyl, $(C_1$-$C_4)$-haloalkylsulfonyl, $(C_1$-$C_4)$-alkylsulfonyloxy, $(C_1$-$C_4)$-alkylcarbonyl, $(C_1$-$C_4)$-haloalkylcarbonyl, aminocarbonyl, $(C_1$-$C_4)$-alkylaminocarbonyl, di-$(C_1$-$C_4)$-alkylaminocarbonyl, $(C_1$-$C_4)$-alkylsulfonylamino, $(C_1$-$C_4)$-alkylamino, di-$(C_1$-$C_4)$-alkylamino, aminosulfonyl, $(C_1$-$C_4)$-alkylaminosulfonyl or di-$(C_1$-$C_4)$-alkylaminosulfonyl, or A represents —O—$CF_2$—O— and, together with $Q^1$ and the carbon atom to which it is attached, forms a five-membered ring where $Q^1$ represents carbon, W represents halogen or $S(O)_nR^8$, where $R^8$ represents $(C_1$-$C_6)$-alkyl, $(C_1$-$C_6)$-cyanoalkyl, $(C_1$-$C_6)$-alkoxy-$(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl, $(C_2$-$C_6)$-haloalkynyl or $(C_3$-$C_8)$-cycloalkyl and n represents 0, 1 or 2, V represents $(C_1$-$C_6)$-alkyl, $(C_1$-$C_6)$-haloalkyl, $(C_1$-$C_6)$-cyanoalkyl, $(C_1$-$C_6)$-alkoxy-$(C_1$-$C_6)$-alkyl, $(C_1$-$C_6)$-haloalkoxy-$(C_1$-$C_6)$-alkyl, $(C_2$-$C_6)$-alkenyl, $(C_2$-$C_6)$-alkenyloxy-$(C_1$-$C_6)$-alkyl, $(C_2$-$C_6)$-haloalkenyloxy-$(C_1$-$C_6)$-alkyl, $(C_2$-$C_6)$-haloalkenyl, $(C_2$-$C_6)$-cyanoalkenyl, $(C_2$-$C_6)$-alkynyl, $(C_2$-$C_6)$-alkynyloxy-$(C_1$-$C_6)$-alkyl, $(C_2$-$C_6)$-haloalkynyloxy-$(C_1$-$C_6)$-alkyl, $(C_2$-$C_6)$-haloalkynyl, $(C_2$-$C_6)$-cyanoalkynyl, $(C_3$-$C_8)$-cycloalkyl, $(C_3$-$C_8)$-cycloalkyl-$(C_3$-$C_8)$-cycloalkyl, $(C_1$-$C_6)$-alkyl-$(C_3$-$C_8)$-cycloalkyl, halo-$(C_3$-$C_8)$-cycloalkyl, cyano-$(C_3$-$C_8)$-cycloalkyl, $(C_1$-$C_6)$-alkylthio-$(C_1$-$C_6)$-alkyl, $(C_1$-$C_6)$-haloalkylthio-$(C_1$-$C_6)$-alkyl, $(C_1$-$C_6)$-alkylsulfinyl-$(C_1$-$C_6)$-alkyl, $(C_1$-$C_6)$-haloalkylsulfinyl-$(C_1$-$C_6)$-alkyl, $(C_1$-$C_6)$-alkylsulfonyl-$(C_1$-$C_6)$-alkyl, $(C_1$-$C_6)$-haloalkylsulfonyl-$(C_1$-$C_6)$-alkyl, $(C_1$-$C_6)$-alkylcarbonyl-$(C_1$-$C_6)$-alkyl, $(C_1$-$C_6)$-haloalkylcarbonyl-$(C_1$-$C_6)$-alkyl, $(C_1$-$C_6)$-alkoxycarbonyl-$(C_1$-$C_6)$-alkyl or $(C_1$-$C_6)$-haloalkoxycarbonyl-$(C_1$-$C_6)$-alkyl and Y represents hydrogen, halogen, cyano, nitro, $(C_1$-$C_4)$-alkyl, $(C_1$-$C_4)$-haloalkyl, $(C_1$-$C_4)$-alkoxy, $(C_1$-$C_4)$-haloalkoxy, $(C_1$-$C_4)$-alkylthio, $(C_1$-$C_4)$-haloalkylthio, $(C_1$-$C_4)$-alkylsulfinyl, $(C_1$-$C_4)$-haloalkylsulfinyl, $(C_1$-$C_4)$-alkylsulfonyl, $(C_1$-$C_4)$-haloalkylsulfonyl, SCN, $(C_1$-$C_4)$-alkylcarbonyl, $(C_1$-$C_4)$-haloalkylcarbonyl, $(C_1$-$C_4)$-alkoxycarbonyl, $(C_1$-$C_4)$-haloalkoxycarbonyl, aminocarbonyl, $(C_1$-$C_4)$-alkylaminocarbonyl, di-$(C_1$-$C_4)$-alkylaminocarbonyl, $(C_1$-$C_4)$-haloalkylaminocarbonyl, $(C_3$-$C_6)$-cycloalkylaminocarbonyl, aminothiocarbonyl, $(C_1$-$C_4)$-alkylaminothiocarbonyl, di-$(C_1$-$C_4)$-alkylaminothiocarbonyl, $(C_1$-$C_4)$-haloalkylaminothiocarbonyl, $(C_3$-$C_6)$-cycloalkylaminothiocarbonyl, amino, $(C_1$-$C_4)$-alkylamino, $(C_1$-$C_4)$-haloalkylamino, di-$(C_1$-$C_4)$-alkylamino, $(C_3$-$C_6)$-cycloalkylamino, $(C_1$-$C_4)$-alkylsulfonylamino, $(C_1$-$C_4)$-alkylcarbonylamino, $(C_1$-$C_4)$-haloalkylcarbonylamino, $(C_1$-$C_4)$-alkylcarbonyl-$(C_1$-$C_4)$-alkylamino, $(C_1$-$C_4)$-haloalkylcarbonyl-$(C_1$-$C_4)$-alkylamino, $(C_3$-$C_6)$-cycloalkylcarbonylamino, $(C_3$-$C_6)$-cycloalkylcarbonyl-$(C_1$-$C_4)$-alkylamino, $(C_1$-$C_4)$-alkylthiocarbonylamino, $(C_1$-$C_4)$-haloalkylthiocarbonylamino, $(C_1$-$C_4)$-alkylthiocarbonyl-$(C_1$-$C_4)$-alkylamino, $(C_1$-$C_4)$-haloalkylthiocarbonyl-$(C_1$-$C_4)$-alkylamino, $(C_3$-$C_6)$-cycloalkylthiocarbonylamino, $(C_3$-$C_6)$-cycloalkylthiocarbonyl-$(C_1$-$C_4)$-alkylamino, $(C_2$-$C_4)$-alkenyl, $(C_2$-$C_4)$-haloalkenyl, $(C_2$-$C_4)$-cyanoalkenyl, $(C_3$-$C_6)$-cycloalkyl-$(C_2)$-alkenyl, $(C_2$-$C_4)$-alkynyl or $(C_2$-$C_4)$-haloalkynyl, or represents $(C_3$-$C_6)$-cycloalkyl or $(C_5$-$C_6)$-cycloalkenyl, each of which is optionally mono- or polysubstituted by identical or different substituents, possible substituents being in each case: $(C_3$-$C_6)$-cycloalkyl, $(C_1$-$C_4)$-alkyl, $(C_1$-$C_4)$-haloalkyl, $(C_1$-$C_4)$-alkoxy, $(C_1$-$C_4)$-haloalkoxy, aminocarbonyl, aminothiocarbonyl, halogen or cyano, or represents aryl or hetaryl, each of which is optionally mono- or polysubstituted by identical or different substituents, where (in the case of hetaryl) optionally at least one carbonyl group may be present and where possible substituents in each case are as follows: cyano, carboxyl, halogen, nitro, acetyl, hydroxy, amino, SCN, $SF_5$, tri-$(C_1$-$C_4)$-alkylsilyl, $(C_3$-$C_6)$-cycloalkyl, $(C_3$-$C_6)$-cycloalkyl-$(C_3$-$C_6)$-cycloalkyl, $(C_1$-$C_4)$-alkyl-$(C_3$-$C_6)$-cycloalkyl, $(C_1$-$C_4)$-haloalkyl-$(C_3$-$C_6)$-cycloalkyl, halo-$(C_3$-$C_6)$-cycloalkyl, cyano-$(C_3$-$C_6)$-cycloalkyl, $(C_1$-$C_4)$-alkyl, $(C_1$-$C_4)$-haloalkyl, $(C_1$-$C_4)$-cyanoalkyl, $(C_1$-$C_4)$-hydroxyalkyl, hydroxycarbonyl-$(C_1$-$C_4)$-alkoxy, $(C_1$-$C_4)$-alkoxycarbonyl-$(C_1$-$C_4)$-alkyl, $(C_1$-$C_4)$-alkoxy-$(C_1$-$C_4)$-alkyl, $(C_2$-$C_4)$-alkenyl, $(C_2$-$C_4)$-haloalkenyl, $(C_2$-$C_4)$-cyanoalkenyl, $(C_3$-$C_6)$-cycloalkyl-$(C_2)$-alkenyl, $(C_2$-$C_4)$-alkynyl, $(C_2$-$C_4)$-haloalkynyl, $(C_2$-$C_4)$-cyanoalkynyl, $(C_1$-$C_4)$-alkoxy, $(C_1$-$C_4)$-haloalkoxy, $(C_1$-$C_4)$-cyanoalkoxy, $(C_1$-$C_4)$-alkoxycarbonyl-$(C_1$-$C_4)$-alkoxy, $(C_1$-$C_4)$-alkoxy-$(C_1$-$C_4)$-alkoxy, $(C_1$-$C_4)$-alkoxyimino, $(C_1$-$C_4)$-haloalkoxyimino, $(C_1$-$C_4)$-alkylthio, $(C_1$-$C_4)$-haloalkylthio, $(C_1$-$C_4)$-alkoxy-$(C_1$-$C_4)$-alkylthio, $(C_1$-$C_4)$-alkylthio-$(C_1$-$C_4)$-alkyl, $(C_1$-$C_4)$-alkylsulfinyl, $(C_1$-$C_4)$-haloalkylsulfinyl, $(C_1$-$C_4)$-alkoxy-$(C_1$-$C_4)$-alkylsulfinyl, $(C_1$-$C_4)$-alkylsulfinyl-$(C_1$-$C_4)$-alkyl, $(C_1$-$C_4)$-alkylsulfonyl, $(C_1$-$C_4)$-haloalkylsulfonyl, $(C_1$-$C_4)$-alkoxy-$(C_1$-$C_4)$-alkylsulfonyl, $(C_1$-$C_4)$-alkylsulfonyl-$(C_1$-$C_4)$-alkyl, $(C_1$-$C_4)$-alkylsulfonyloxy, $(C_1$-$C_4)$-haloalkylsulfonyloxy, $(C_1$-$C_4)$-alkylcarbonyl, $(C_1$-$C_4)$-haloalkylcarbonyl, $(C_1$-$C_4)$-alkylcarbonyloxy, $(C_1$-$C_4)$-alkoxycarbonyl, $(C_1$-$C_4)$-haloalkoxycarbonyl, aminocarbonyl, $(C_1$-$C_4)$-alkylaminocarbonyl, $(C_1$-$C_4)$-haloalkylaminocarbonyl, di-$(C_1$-$C_4)$-alkylaminocarbonyl, $(C_2$-$C_4)$-alkenylaminocarbonyl, di-$(C_2$-$C_4)$-alkenylaminocarbonyl, $(C_3$-$C_6)$-cycloalkylaminocarbonyl, $(C_1$-$C_4)$-alkylsulfonylamino, $(C_1$-$C_4)$-alkylamino, di-$(C_1$-$C_4)$-alkylamino, $(C_1$-$C_4)$-haloalkylamino, $(C_3$-$C_6)$-cycloalkylamino, aminosulfonyl, $(C_1$-$C_4)$-alkylaminosulfonyl, di-$(C_1$-$C_4)$-alkylaminosulfonyl, $(C_1$-$C_4)$-alkylsulfoximino, aminothiocarbonyl, $(C_1$-$C_4)$-alkylaminothiocarbonyl, di-$(C_1$-$C_4)$-alkylaminothiocarbonyl, $(C_1-C_4)$-haloalkylaminothiocarbonyl, $(C_3-C_6)$-cycloalkylaminothiocarbonyl, $(C_1-C_4)$-alkylcarbonylamino, $(C_1-C_4)$-haloalkylcarbonylamino, $(C_1-C_4)$-alkylcarbonyl-$(C_1-C_4)$-alkylamino, $(C_1-C_4)$-haloalkylcarbonyl-$(C_1-C_4)$-alkylamino, $(C_3-C_6)$-cycloalkylcarbonylamino, $(C_3-C_6)$-cycloalkylcarbonyl-$(C_1-C_4)$-alkylamino, $(C_1-C_4)$-alkylthiocarbonylamino, $(C_1-C_4)$-haloalkylthiocarbonylamino, $(C_1-C_4)$-alkylthiocarbonyl-$(C_1-C_4)$-alkylamino, $(C_1-C_4)$-haloalkylthiocarbonyl-$(C_1-C_4)$-alkylamino, $(C_3-C_6)$-cycloalkylthiocarbonylamino, $(C_3-C_6)$-cycloalkylthiocarbonyl-$(C_1-C_4)$-alkylamino, hetaryl, oxohetaryl, halohetaryl, halooxohetaryl, cyanohetaryl, cyanooxohetaryl, $(C_1-C_4)$-haloalkylhetaryl or $(C_1-C_4)$-haloalkyloxohetaryl, characterized in that, in a first process step a), a compound Q-H in which Q is as defined above is reacted with an organozinc base of the structure $(NR^3R^4)$—Zn—$R^2$ or $(NR^3R^4)_2$—Zn in which $R^2$ represents halogen or —O-pivaloyl and $R^3$ and $R^4$ together form a $—(CH_2)_4—$, $—(CH_2)_5—$ or $—(CH_2)_2O(CH_2)_2—$ group, where each of these groups may optionally be substituted by 1, 2, 3 or 4 $R^5$ radicals and $R^5$ is selected from the group consisting of methyl, ethyl, n-propyl and i-propyl, to give a compound of the formula (IIIa) or the formula (IIIb)

(IIIa)

(IIIb)

in which Q and $R^2$ each have the definitions given above, and this compound of the formula (IIIa) or (IIIb) is reacted in a second process step b) with a compound of the formula (I)

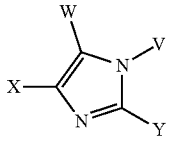

(I)

in which X represents halogen and V, W and Y each have the meanings mentioned above, in the presence of a catalyst, to give the compound of the formula (II).

DETAILED DESCRIPTION OF A PREFERRED EMBODIMENT

Preferably, at most four of the variables $Q^1$, $Q^2$, $Q^3$, $Q^4$, $Q^5$, $Q^6$ and $Q^7$ simultaneously represent nitrogen. Here, nitrogen is to be understood as meaning N and/or $NR^7$.

Preferred and particularly preferred definitions of the Q, V, W, $R^1$, $R^2$, X and Y radicals included in the aforementioned formulae (I), (II), (IIIa) and (IIIb) of the process of the invention are elucidated hereinafter, with more specific description of the organozinc base further down, and so the preferred configurations of the base are specified at that point.

(Configuration 2)

Q preferably represents a structural element from the group of Q1 to Q14,

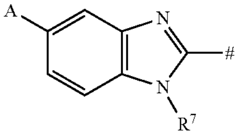

Q1

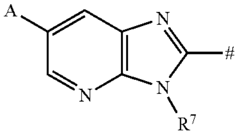

Q2

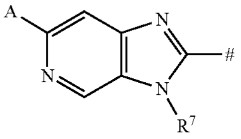

Q3

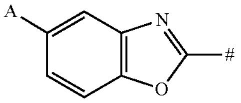

Q4

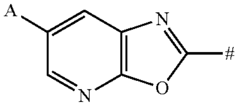

Q5

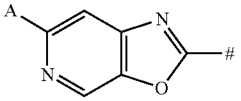

Q6

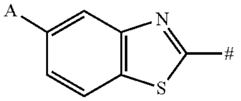

Q7

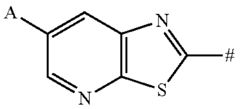

Q8

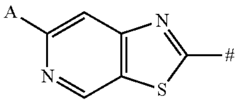

Q9

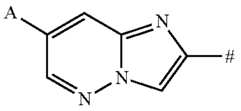

Q10

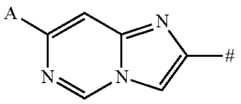

Q11

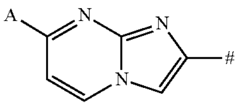

Q12

-continued

Q13

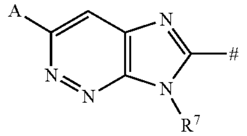

Q14

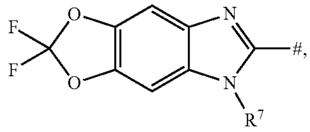

where $R^7$ preferably represents ($C_1$-$C_4$)-alkyl, ($C_1$-$C_4$)-haloalkyl, ($C_1$-$C_4$)-alkoxy-($C_1$-$C_4$)-alkyl, ($C_1$-$C_4$)-haloalkoxy-($C_1$-$C_4$)-alkyl, ($C_1$-$C_4$)-alkylthio-($C_1$-$C_4$)-alkyl, ($C_1$-$C_4$)-alkylsulfinyl-($C_1$-$C_4$)-alkyl, ($C_1$-$C_4$)-alkylsulfonyl-($C_1$-$C_4$)-alkyl or ($C_1$-$C_4$)-alkylcarbonyl-($C_1$-$C_4$)-alkyl, and A preferably represents fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulfinyl or trifluoromethylsulfonyl, W preferably represents halogen or $S(O)_nR^8$, where $R^8$ preferably represents ($C_1$-$C_6$)-alkyl, ($C_1$-$C_4$)-cyanoalkyl, ($C_1$-$C_4$)-alkoxy-($C_1$-$C_4$)-alkyl, ($C_1$-$C_6$)-haloalkyl, ($C_2$-$C_4$)-alkenyl, ($C_2$-$C_4$)-haloalkenyl, ($C_2$-$C_4$)-alkynyl, ($C_2$-$C_4$)-haloalkynyl or ($C_3$-$C_6$)-cycloalkyl and n preferably represents 0, 1 or 2, $R^2$ preferably represents halogen, in particular chlorine, bromine or iodine, X preferably represents halogen, in particular bromine or iodine, V preferably represents ($C_1$-$C_6$)-alkyl, ($C_1$-$C_4$)-haloalkyl, ($C_1$-$C_4$)-cyanoalkyl, ($C_1$-$C_4$)-alkoxy-($C_1$-$C_4$)-alkyl, ($C_1$-$C_4$)-haloalkoxy-($C_1$-$C_4$)-alkyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, halo-($C_3$-$C_6$)-cycloalkyl, cyano-($C_3$-$C_6$)-cycloalkyl, ($C_1$-$C_4$)-alkylthio-($C_1$-$C_4$)-alkyl, ($C_1$-$C_4$)-haloalkylthio-($C_1$-$C_4$)-alkyl, ($C_1$-$C_4$)-alkylsulfinyl-($C_1$-$C_4$)-alkyl, ($C_1$-$C_4$)-haloalkylsulfinyl-($C_1$-$C_4$)-alkyl, ($C_1$-$C_4$)-alkylsulfonyl-($C_1$-$C_4$)-alkyl or ($C_1$-$C_4$)-haloalkylsulfonyl-($C_1$-$C_4$)-alkyl and Y preferably represents hydrogen, halogen, cyano, ($C_1$-$C_4$)-alkyl, ($C_1$-$C_4$)-haloalkyl, ($C_1$-$C_4$)-alkoxy, ($C_1$-$C_4$)-haloalkoxy, aminocarbonyl, ($C_1$-$C_4$)-alkylaminocarbonyl, di-($C_1$-$C_4$)-alkylaminocarbonyl, ($C_1$-$C_4$)-haloalkylaminocarbonyl, ($C_3$-$C_6$)-cycloalkylaminocarbonyl, amino, ($C_1$-$C_4$)-alkylamino, ($C_1$-$C_4$)-haloalkylamino, di-($C_1$-$C_4$)-alkylamino, ($C_3$-$C_6$)-cycloalkylamino, ($C_1$-$C_4$)-alkylsulfonylamino, ($C_1$-$C_4$)-alkylcarbonylamino, ($C_1$-$C_4$)-haloalkylcarbonylamino, ($C_1$-$C_4$)-alkylcarbonyl-($C_1$-$C_2$)-alkylamino, ($C_1$-$C_4$)-haloalkylcarbonyl-($C_1$-$C_2$)-alkylamino, ($C_3$-$C_6$)-cycloalkylcarbonylamino, ($C_3$-$C_6$)-cycloalkylcarbonyl-($C_1$-$C_2$)-alkylamino, ($C_2$-$C_4$)-alkenyl, ($C_2$-$C_4$)-haloalkenyl, ($C_2$-$C_4$)-cyanoalkenyl or ($C_3$-$C_6$)-cycloalkyl-($C_2$)-alkenyl, or represents ($C_3$-$C_6$)-cycloalkyl or ($C_5$-$C_6$)-cycloalkenyl, each of which is optionally mono- or polysubstituted by identical or different substituents, possible substituents being in each case: ($C_3$-$C_6$)-cycloalkyl, ($C_1$-$C_4$)-alkyl, ($C_1$-$C_4$)-haloalkyl, ($C_1$-$C_4$)-alkoxy, ($C_1$-$C_4$)-haloalkoxy, halogen or cyano, or represents phenyl, pyridyl, pyrimidyl, pyridazinyl, thiophenyl, furanyl, pyrazolyl, pyrrolyl, thiazolyl, oxazolyl or imidazolyl, each of which is optionally mono- or polysubstituted by identical or different substituents, possible substituents being in each case: cyano, halogen, nitro, acetyl, hydroxy, amino, $SF_5$—, ($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_2$)-alkyl, ($C_2$-$C_4$)-alkenyl, ($C_2$-$C_4$)-haloalkenyl, ($C_2$-$C_4$)-cyanoalkenyl, ($C_3$-$C_6$)-cycloalkyl-($C_2$)-alkenyl, ($C_2$-$C_4$)-alkynyl, ($C_2$-$C_4$)-haloalkynyl, ($C_2$-$C_4$)-cyanoalkynyl, ($C_1$-$C_4$)-alkoxy, ($C_1$-$C_4$)-haloalkoxy, ($C_1$-$C_4$)-cyanoalkoxy, ($C_1$-$C_4$)-alkoxy-($C_1$-$C_2$)-alkoxy, ($C_1$-$C_4$)-alkoxyimino, ($C_1$-$C_4$)-haloalkoxyimino, ($C_1$-$C_4$)-alkylthio, ($C_1$-$C_4$)-haloalkylthio, ($C_1$-$C_4$)-alkylthio-($C_1$-$C_2$)-alkyl, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, ($C_1$-$C_4$)-haloalkylsulfonyloxy, ($C_1$-$C_4$)-alkylcarbonyl, ($C_1$-$C_4$)-haloalkylcarbonyl, aminocarbonyl, ($C_1$-$C_4$)-alkylaminocarbonyl, ($C_1$-$C_4$)-haloalkylaminocarbonyl, di-($C_1$-$C_4$)-alkylaminocarbonyl, ($C_3$-$C_6$)-cycloalkylaminocarbonyl, aminothiocarbonyl, ($C_1$-$C_4$)-alkylaminothiocarbonyl, di-($C_1$-$C_4$)-alkylaminothiocarbonyl, ($C_1$-$C_4$)-haloalkylaminothiocarbonyl, ($C_3$-$C_6$)-cycloalkylaminothiocarbonyl, ($C_1$-$C_4$)-alkylsulfonylamino, ($C_1$-$C_4$)-alkylamino, di-($C_1$-$C_4$)-alkylamino, ($C_1$-$C_4$)-haloalkylamino, ($C_3$-$C_6$)-cycloalkylamino, aminosulfonyl, ($C_1$-$C_4$)-alkylaminosulfonyl, di-($C_1$-$C_4$)-alkylaminosulfonyl, ($C_1$-$C_4$)-alkylcarbonylamino, ($C_1$-$C_4$)-haloalkylcarbonylamino, ($C_1$-$C_4$)-alkylcarbonyl-($C_1$-$C_2$)-alkylamino, ($C_1$-$C_2$)-haloalkylcarbonyl-($C_1$-$C_2$)-alkylamino, ($C_3$-$C_6$)-cycloalkylcarbonylamino, ($C_3$-$C_6$)-cycloalkylcarbonyl-($C_1$-$C_2$)-alkylamino, ($C_1$-$C_4$)-alkylthiocarbonylamino, ($C_1$-$C_4$)-haloalkylthiocarbonylamino, ($C_1$-$C_4$)-alkylthiocarbonyl-($C_1$-$C_2$)-alkylamino, ($C_1$-$C_4$)-haloalkylthiocarbonyl-($C_1$-$C_2$)-alkylamino, ($C_3$-$C_6$)-cycloalkylthiocarbonylamino or ($C_3$-$C_6$)-cycloalkylthiocarbonyl-($C_1$-$C_2$)-alkylamino.

(Configuration 3)

Q particularly preferably represents a structural element from the group of Q2, Q3, Q4, Q10, Q11, Q13 and Q14, where $R^7$ particularly preferably represents ($C_1$-$C_4$)-alkyl or ($C_1$-$C_4$)-alkoxy-($C_1$-$C_4$)-alkyl and A particularly preferably represents bromine, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethylthio, trifluoromethylsulfinyl or trifluoromethylsulfonyl, W particularly preferably represents halogen or $S(O)_nR^8$, where $R^8$ particularly preferably represents methyl, ethyl, n-propyl or isopropyl, and n particularly preferably represents 0, 1 or 2, $R^2$ particularly preferably represents chlorine, X particularly preferably represents bromine or iodine, in particular iodine, V particularly preferably represents methyl, ethyl, n-propyl or isopropyl, and Y particularly preferably represents hydrogen, bromine, iodine, cyano, ethenyl, cyclopropylethenyl, isopropenyl, cyclopropylethynyl, methyl, ethyl, isopropyl, cyclopropylethyl, methoxycarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl, dimethylaminothiocarbonyl, or represents cyclopropyl, cyclobutyl, cyclopentyl, cyclohexyl, cyclopentenyl or cyclohexenyl, each of which is optionally mono- or disubstituted by identical or different substituents, possible substituents being in each case: methyl, ethyl, n-propyl, isopropyl, cyclopropyl, difluoromethyl, trifluoromethyl, cyano, fluorine or chlorine, or represents phenyl, pyridin-2-yl, pyridin-3-yl, pyridin-4-yl, pyrimidin-5-yl, pyridazin-3-yl, pyridazin-4-yl, thien-2-yl, thien-3-yl, 1,3-thiazol-5-yl, 1H-imidazol-1-yl, 1H-imidazol-2-yl, 1H-imidazol-5-yl, 1H-pyrazol-1-yl, 1H-pyrazol-3-yl, 1H-pyrazol-4-yl, 1H-pyrazol-5-yl, 1H-pyrrol-1-yl, 1H-pyrrol-2-yl, 1H-pyrrol-3-yl or 1-cyclohexenyl, each of which is optionally mono-, di- or trisubstituted by identical or different substituents, possible substituents being in each case: cyano, fluorine, chlorine, methyl, cyclopropyl, cyanomethyl, cyanoisopropyl, cyanocyclopropyl, trifluoromethyl, trifluoroethyl or aminocarbonyl.

(Configuration 4)

Q very particularly preferably represents the structural element Q2, Q3 or Q13, where $R^7$ very particularly preferably represents methyl, ethyl, n-propyl or isopropyl, in particular methyl, and A very particularly preferably represents bromine, trifluoromethyl, pentafluoroethyl or trifluoromethylthio, W very particularly preferably represents $S(O)_nR^8$, where $R^8$ very particularly preferably represents ethyl and n very particularly preferably represents 0 or 2, $R^2$ very particularly preferably represents chlorine, X very particularly preferably represents iodine, V very particularly preferably represents methyl and Y very particularly preferably represents hydrogen, bromine, cyclopropyl, para-chlorophenyl, 5-chlorothien-2-yl or 5-chloro-2-pyridine.

The radical definitions and elucidations given above apply both to the end products and intermediates and to the starting materials in a corresponding manner. These radical definitions can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Very particular preference is given in accordance with the invention to those compounds in which there is a combination of the definitions listed above as being most preferred.

In a further preferred embodiment of the invention, Q represents Q1 and $R^7$, A, W, $R^2$, X, V and Y have the meanings given in Configuration 1 or those given in Configuration 2 or those given in Configuration 3 or those given in Configuration 4 (Configuration 5).

In a further preferred embodiment of the invention, Q represents Q2 and $R^7$, A, W, $R^2$, X, V and Y have the meanings given in Configuration 1 or those given in Configuration 2 or those given in Configuration 3 or those given in Configuration 4 (Configuration 6).

In a further preferred embodiment of the invention, Q represents Q3 and $R^7$, A, W, $R^2$, X, V and Y have the meanings given in Configuration 1 or those given in Configuration 2 or those given in Configuration 3 or those given in Configuration 4 (Configuration 7).

In a further preferred embodiment of the invention, Q represents Q4 and A, W, $R^2$, X, V and Y have the meanings given in Configuration 1 or those given in Configuration 2 or those given in Configuration 3 or those given in Configuration 4 (Configuration 8).

In a further preferred embodiment of the invention, Q represents Q5 and A, W, $R^2$, X, V and Y have the meanings given in Configuration 1 or those given in Configuration 2 or those given in Configuration 3 or those given in Configuration 4 (Configuration 9).

In a further preferred embodiment of the invention, Q represents Q6 and A, W, $R^2$, X and Y have the meanings given in Configuration 1 or those given in Configuration 2 or those given in Configuration 3 or those given in Configuration 4 (Configuration 10).

In a further preferred embodiment of the invention, Q represents Q7 and A, W, $R^2$, X, V and Y have the meanings given in Configuration 1 or those given in Configuration 2 or those given in Configuration 3 or those given in Configuration 4 (Configuration 11).

In a further preferred embodiment of the invention, Q represents Q8 and A, W, $R^2$, X, V and Y have the meanings given in Configuration 1 or those given in Configuration 2 or those given in Configuration 3 or those given in Configuration 4 (Configuration 12).

In a further preferred embodiment of the invention, Q represents Q9 and A, W, $R^2$, X, V and Y have the meanings given in Configuration 1 or those given in Configuration 2 or those given in Configuration 3 or those given in Configuration 4 (Configuration 13).

In a further preferred embodiment of the invention, Q represents Q10 and A, W, $R^2$, X, V and Y have the meanings given in Configuration 1 or those given in Configuration 2 or those given in Configuration 3 or those given in Configuration 4 (Configuration 14).

In a further preferred embodiment of the invention, Q represents Q11 and A, W, $R^2$, X and Y have the meanings given in Configuration 1 or those given in Configuration 2 or those given in Configuration 3 or those given in Configuration 4 (Configuration 15).

In a further preferred embodiment of the invention, Q represents Q12 and A, W, $R^2$, X, V and Y have the meanings given in Configuration 1 or those given in Configuration 2 or those given in Configuration 3 or those given in Configuration 4 (Configuration 16).

In a further preferred embodiment of the invention, Q represents Q13 and $R^7$, A, W, $R^2$, X, V and Y have the meanings given in Configuration 1 or those given in Configuration 2 or those given in Configuration 3 or those given in Configuration 4 (Configuration 17).

In a further preferred embodiment of the invention, Q represents Q14 and $R^7$, W, $R^2$, X, V and Y have the meanings given in Configuration 1 or those given in Configuration 2 or those given in Configuration 3 or those given in Configuration 4 (Configuration 18).

In a particularly preferred embodiment of the invention, Q represents Q2, Q3, Q4, Q10, Q11, Q13 or Q14 and $R^7$, A, W, $R^2$, X, V and Y have the meanings given in Configuration 1 or those given in Configuration 2 or those given in Configuration 4 (Configuration 19).

In a very particularly preferred embodiment of the invention, Q represents Q2, Q3 or Q13 and $R^7$, A, W, $R^2$, X, V and Y have the meanings given in Configuration 1 or those given in Configuration 2 or those given in Configuration 3 (Configuration 20).

In a further preferred embodiment of the invention, W represents $S(O)_nR^8$ and Q, n, $R^7$, $R^8$, A, $R^2$, X, V and Y have the meanings given in Configuration 1 or those given in Configuration 2 or those given in Configuration 3 or those given in Configuration 4 (Configuration 21).

Advantageously, the imidazole derivatives of the formula (II) can be prepared by the process according to the invention with good yields and in high purity. A great advantage of the process according to the invention is the regioselectivity thereof. Because of the very good functional group tolerance of zinc reagents, zinc bases are very attractive. Especially advantageous is moreover the possibility of being able to conduct Negishi couplings even at distinctly lower temperatures, in which case even functional groups that are sensitive at higher temperatures, such as esters or fluorine atoms, are tolerated in processes according to the invention without impairing the regioselectivity that exists. Moreover, Negishi cross-couplings within the context of a process according to the invention can also give rise to good yields of target product in the presence of ortho substituents on the imidazole skeleton, even though such couplings with 2-substituted imidazole derivatives have to date been known for giving low yields. Thus, further and/or more flexible derivatizations of reactant and product are possible without having to constantly alter or adapt synthesis routes.

The process according to the invention can be illustrated by the following scheme (I):

Scheme (I)

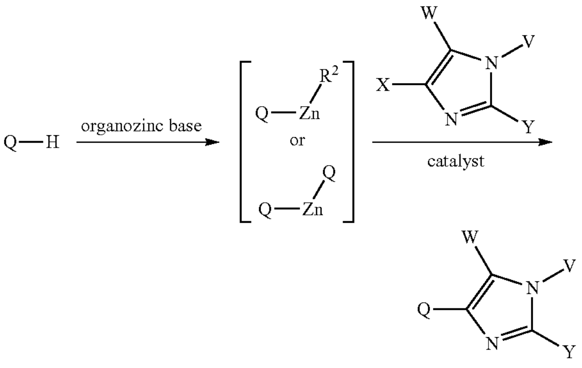

Here, Q, W, $R^2$, X, V and Y and, within the respective definitions, any further structural elements present each have the definitions given above. The compounds shown in brackets are the intermediate (formula IIIa or formula IIIb) which is reacted further with a compound of the formula (I) to give the compound of the formula (II). Accordingly, the process according to the invention can be divided into the two process steps a) and b), step a) being the conversion of the compound Q-H to the respective intermediate and step b) being the further conversion of the intermediate to the compound of the formula (II).

General Definitions

In the context of the present invention, the term halogen (Hal), unless defined otherwise, encompasses those elements selected from the group consisting of fluorine, chlorine, bromine and iodine.

The term "halides" in connection with the present invention describes compounds between halogens and elements of other groups of the Periodic Table, where halide salts (ionic compounds (salts) which consist of anions and cations because of the great difference in electronegativity between the elements involved and are held together by electrostatic interactions) or covalent halides (covalent compounds where the difference in electronegativity is not as great as in the aforementioned ionic compounds, but the bonds have charge polarity) may be present, depending on the nature of the chemical bond. Particular preference is given in accordance with the invention to halide salts.

The term "pivaloyl" in the context of the present invention describes the deprotonated radical of pivalic acid (X) having the empirical formula $(CH_3)_3CCO_2H$.

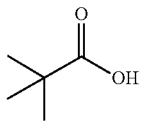

(X)

"O-pivaloyl" correspondingly means that the pivaloyl radical is attached via the deprotonated oxygen atom of the acid group.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, particular preference is given to $C_1$-$C_6$-alkyl radicals. Particular preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood to mean in the present case an O-alkyl radical, where the term "alkyl" is as defined above.

According to the invention, unless defined differently elsewhere, the term "aryl" is understood to mean an aromatic radical having 6 to 14 carbon atoms, preferably phenyl, naphthyl, anthryl or phenanthrenyl, particularly preferably phenyl.

Unless defined differently elsewhere, the term "arylalkyl" is understood to mean a combination of the radicals "aryl" and "alkyl" defined according to the invention, where the radical is generally attached via the alkyl group. Examples of these are benzyl, phenylethyl or α-methylbenzyl, benzyl being particularly preferred.

Unless defined differently elsewhere, "hetaryl" or "heteroaromatic ring" denotes a mono-, bi- or tricyclic heterocyclic group composed of carbon atoms and at least one heteroatom, where at least one ring is aromatic. Preferably, the hetaryl group contains 3, 4, 5, 6, 7 or 8 carbon atoms. Particular preference is given here to monocyclic groups of 3, 4, 5, 6, 7 or 8 carbon atoms and at least one heteroatom. The hetaryl group is particularly preferably selected from the series furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl, imidazopyridinyl and indolizinyl.

Halogen-substituted radicals, for example haloalkyl, are mono- or polyhalogenated, up to the maximum number of possible substituents. In the case of polyhalogenation, the halogen atoms may be identical or different. Unless defined differently, halogen here is fluorine, chlorine, bromine or iodine, especially fluorine, chlorine or bromine. Alkyl groups substituted by one or more halogen atoms (-Hal) are, for example, selected from trifluoromethyl ($CF_3$), difluoromethyl ($CHF_2$), $CF_3CH_2$, $ClCH_2$ or $CF_3CCl_2$.

Unless stated otherwise, optionally substituted radicals may be mono- or polysubstituted, where the substituents in the case of polysubstitutions may be the same or different.

The synthesis of compounds Q-H as reactants of a process according to the invention is known in principle to those skilled in the art. For example, compounds Q-H where Q=Q1, Q2, Q3, Q13 or Q14 can be obtained from corresponding (het)aryldiamine derivatives by ring closure to give the respective imidazole compound, as described, for example, in WO 2014/100065 or WO 2015/017610 preferably under acidic conditions. Alternative syntheses are likewise possible, but are more complex and as a result generally less economically advantageous. The compounds Q-H where Q=Q4, Q5 or Q6 can be prepared, for example, from corresponding (het)arylamino alcohol derivatives by ring closure with an orthoformate to give the respective oxazole compound, for example as in WO 2018/037223. The compounds Q-H where Q=Q7, Q8 or Q9 can be prepared, for example, from corresponding (het)arylaminohalogen derivatives by ring closure with an O-alkyl carbonothioate and subsequent decarboxylation to give the respective thiazole compound, for example as in WO 2013/066729. The compounds Q-H where Q=Q10, Q11 or Q12 can be prepared, for example, from corresponding (het)arylamino derivatives by ring closure with a haloacetaldehyde to give the respective imidazole compound, for example as in WO 2003/099816, WO 2010/083145 or *Organic Process Research & Development* 2006, 10, 398-402.

The conversion of the compounds Q-H to compounds of the formula (IIIa) or (IIIb) in the first process step (step a)) is effected in the presence of an organozinc base of the structure ($NR^3R^4$)—Zn—$R^2$ or $(NR^3R^4)_2$—Zn, in which (Configuration B-1)

$R^2$ is as defined above (Configuration 1) (and is therefore halogen or —O-pivaloyl), $R^3$ and $R^4$ together form a $—(CH_2)_4—$, $—(CH_2)_5—$ or $—(CH_2)_2O(CH_2)_2—$ group, where each of these groups may optionally be substituted by 1, 2, 3 or 4 $R^5$ radicals and $R^5$ is selected from the group consisting of methyl, ethyl, n-propyl and i-propyl.

It is preferable that (Configuration B-2)

$R^2$ is as defined above as preferred (Configuration 2) (and is therefore halogen, especially chlorine, bromine or iodine), $R^3$ and $R^4$ together form a $—(CH_2)_5—$ group, where each of these groups may optionally be substituted by 1, 2, 3 or 4 $R^5$ radicals and $R^5$ is selected from the group consisting of methyl and ethyl.

It is particularly preferable that (Configuration B-3)

$R^2$ is as defined above as more preferred (Configuration 3) or as most preferred (Configuration 4) (and is therefore chlorine) and $R^3$ and $R^4$ together form a $—(CH_2)_5—$ group substituted by 4 methyl groups.

The radical definitions given above can be combined with one another as desired, i.e. including combinations between the respective preferred ranges.

In a very particularly preferred configuration of the base according to the invention, the structural element ($NR^3R^4$) is tetramethylpiperidine (TMP) of formula (IV).

(IV)

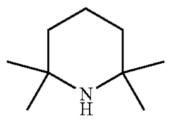

Organozinc bases very particularly preferred in accordance with the invention are accordingly characterized in that zinc is bound to TMP, especially in the form of zinc halide and most preferably in the form of zinc chloride. Bases of this kind have the following structure of the formula (V) (Configuration B-4)

$$(TMP)_xZnCl_{2-x}, \quad (V)$$

in which x represents the number 1 or 2. Among these, preference is given in turn to bases with x=1 (Configuration B-5) of formula (VI):

(VI)

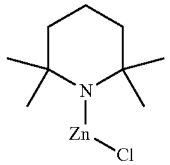

In a further preferred embodiment of the process according to the invention, the organozinc base is present in conjunction with alkali metal or alkaline earth metal halides. This is especially true of bases of the formulae (V) and (VI). Particularly preferred alkali metal halides or alkaline earth metal halides of this kind are lithium chloride and magnesium chloride, very particular preference being given to lithium chloride. Organozinc bases that are very particularly preferred in accordance with the invention are accordingly TMP ZnCl.LiCl or $(TMP)_2Zn.2LiCl$ (Configuration B-6). Most preferred is TMP ZnCl.LiCl (VII; Configuration B-7).

(VII)

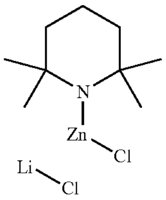

Specific combinations of compounds of the formulae (I), (II) and (IIIa) or (IIIb) with bases according to the invention are cited hereinafter by way of example in Table 1, these being employable in a process according to the invention. Since, in some configurations, the structural element $R^2$ is present both in the base according to the invention and in the compound of the formula (IIIa), the narrowest definition applies to $R^2$ in each case.

TABLE 1

| Number | Compounds of the formulae (I), (II) and (IIIa) or (IIIb) | Base according to |
|---|---|---|
| 1 | Configuration 1 | Configuration B-1 |
| 2 | Configuration 1 | Configuration B-2 |
| 3 | Configuration 1 | Configuration B-3 |
| 4 | Configuration 1 | Configuration B-4 |
| 5 | Configuration 1 | Configuration B-5 |
| 6 | Configuration 1 | Configuration B-6 |
| 7 | Configuration 1 | Configuration B-7 |
| 8 | Configuration 2 | Configuration B-1 |
| 9 | Configuration 2 | Configuration B-2 |
| 10 | Configuration 2 | Configuration B-3 |
| 11 | Configuration 2 | Configuration B-4 |
| 12 | Configuration 2 | Configuration B-5 |
| 13 | Configuration 2 | Configuration B-6 |
| 14 | Configuration 2 | Configuration B-7 |
| 15 | Configuration 3 | Configuration B-1 |
| 16 | Configuration 3 | Configuration B-2 |
| 17 | Configuration 3 | Configuration B-3 |
| 18 | Configuration 3 | Configuration B-4 |
| 19 | Configuration 3 | Configuration B-5 |
| 20 | Configuration 3 | Configuration B-6 |
| 21 | Configuration 3 | Configuration B-7 |
| 22 | Configuration 4 | Configuration B-1 |
| 23 | Configuration 4 | Configuration B-2 |
| 24 | Configuration 4 | Configuration B-3 |
| 25 | Configuration 4 | Configuration B-4 |
| 26 | Configuration 4 | Configuration B-5 |
| 27 | Configuration 4 | Configuration B-6 |
| 28 | Configuration 4 | Configuration B-7 |
| 29 | Configuration 17 | Configuration B-1 |
| 30 | Configuration 17 | Configuration B-2 |
| 31 | Configuration 17 | Configuration B-3 |
| 32 | Configuration 17 | Configuration B-4 |
| 33 | Configuration 17 | Configuration B-5 |
| 34 | Configuration 17 | Configuration B-6 |
| 35 | Configuration 17 | Configuration B-7 |
| 36 | Configuration 19 | Configuration B-1 |
| 37 | Configuration 19 | Configuration B-2 |

TABLE 1-continued

| Number | Compounds of the formulae (I), (II) and (IIIa) or (IIIb) | Base according to |
|---|---|---|
| 38 | Configuration 19 | Configuration B-3 |
| 39 | Configuration 19 | Configuration B-4 |
| 40 | Configuration 19 | Configuration B-5 |
| 41 | Configuration 19 | Configuration B-6 |
| 42 | Configuration 19 | Configuration B-7 |
| 43 | Configuration 20 | Configuration B-1 |
| 44 | Configuration 20 | Configuration B-2 |
| 45 | Configuration 20 | Configuration B-3 |
| 46 | Configuration 20 | Configuration B-4 |
| 47 | Configuration 20 | Configuration B-5 |
| 48 | Configuration 20 | Configuration B-6 |
| 49 | Configuration 20 | Configuration B-7 |
| 50 | Configuration 21 | Configuration B-1 |
| 51 | Configuration 21 | Configuration B-2 |
| 52 | Configuration 21 | Configuration B-3 |
| 53 | Configuration 21 | Configuration B-4 |
| 54 | Configuration 21 | Configuration B-5 |
| 55 | Configuration 21 | Configuration B-6 |
| 56 | Configuration 21 | Configuration B-7 |

Preferably, the organozinc base is used in the process according to the invention in a total amount of 0.5 to 5.0 equivalents, preferably of 0.8 to 2.0 equivalents, further preferably of 1.0 to 1.5 equivalents and more preferably of 1.0 to 1.2 equivalents, based on the compound Q-H. One advantage of the process according to the invention in this regard is that the organometallic base can be used in virtually stoichiometric amounts.

Depending on whether the structural element $(NR^3R^4)$ is present once or twice in the organozinc base used, intermediate compounds of the formula (IIIa) or of the formula (IIIb) are formed in process step a).

The conversion of the compounds of the formula (IIIa) or (IIIb) to compounds of the formula (II) in the second process step b) is carried out in the presence of a compound of the formula (I)

(I)

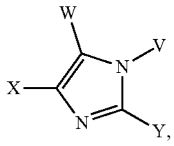

in which X, V, W and Y each have the meanings mentioned above.

The compounds of the formula (I) are preferably chosen such that X is the best leaving group in the molecule. Accordingly, X is preferably bromine or iodine, in particular iodine. In this case, during the Negishi cross-coupling the reaction takes place virtually exclusively at position 4, since X is the best leaving group on the imidazole skeleton. It then regioselectively affords the corresponding imidazole derivative of the formula (II).

Compounds of the formula (I) can be obtained, for example, by selective substitution of a corresponding precursor, i.e. an imidazole derivative in which the radicals W and X represent the same halogen (e.g. iodine). Such a selective substitution can be achieved, for example, by halogen-metal exchange of the precursor in the presence of lithium bases or magnesium bases and subsequent reaction with elemental halogen (e.g. bromine) or a disulfide. Such a halogen-metal exchange is described, for example, in *Bul-*

*letin of the Chemical Society of Japan* 2013, 86, 927-939 or *Journal of Organic Chemistry* 2000, 65, 4618-4634.

Preferably, the compound of the formula (I) is used in the process according to the invention in a total amount of 0.5 to 10 equivalents, preferably of 0.8 to 5.0 equivalents, further preferably of 1.0 to 2.5 equivalents and more preferably of 1.0 to 1.5 equivalents or more preferably of 1.5 to 2.0 equivalents or more preferably of 1.0 to 2.0 equivalents, based on the compound Q-H.

The conversion in process step b) is further effected in the presence of a catalyst. Preferably, the catalyst is a palladium compound or a nickel compound. More preferably, the catalyst is a palladium compound. It is most preferably tetrakis(triphenylphosphine)palladium(0), abbreviated to $Pd(PPh_3)_4$, of the formula (IX).

(IX)

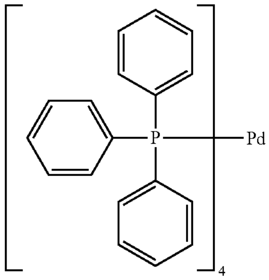

Typically, in a process according to the invention, 2.5-25 mol % and preferably 5-20 mol % of catalyst is used.

The inventive conversion of the compounds Q-H to compounds of the formula (IIIa) or (IIIb) and further to compounds of the formula (II) is preferably effected in the presence of an organic solvent in each case. Useful solvents in principle include all organic solvents which are inert under the reaction conditions employed and in which the compounds to be converted have adequate solubility. Suitable solvents especially include: tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU), halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, especially 1,2-dichlorobenzene, chlorotoluene, trichlorobenzene; 4-methoxybenzene, fluorinated aliphatics and aromatics, such as trichlorotrifluoroethane, benzotrifluoride and 4-chlorobenzotrifluoride. It is also possible to use solvent mixtures, preferably mixtures of the solvents mentioned above such as tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, dimethylformamide (DMF).

Preferred solvents are THF, N,N-dimethylformamide (DMF), 1,4-dioxane, diglyme, methyl tert-butyl ether (MTBE), tert-amyl methyl ether (TAME), 2-methyl-THF, toluene and 4-methoxybenzene.

Particularly preferred solvents are THF and N,N-dimethylformamide (DMF), very particular preference being given to THF.

The solvent may also be degassed (oxygen-free).

Preference is given to using the same solvent for both process steps a) and b). Alternative configurations of the invention in which different solvents are used for process steps a) and b) are likewise possible, however, in which case the solvents are then likewise preferably selected from the aforementioned solvents, and the respective solvents specified as being preferred, particularly preferred and especially preferred are applicable to the respective process step a) or b).

The conversion in method step a) is generally carried out at a temperature between 0° C. and 80° C. and with increasing preference between 10° C. and 70° C., between 15° C. and 60° C., between 20° C. and 50° C., between 20° C. and 40° C., and most preferably between 20° C. and 35° C., for example at room temperature or 25° C.

Step a) generally takes place over a period of 5 min to 12 h, preferably 15 min to 10 h and particularly preferably 30 min to 2 h.

The conversion in process step b) is generally carried out at a temperature between 40° C. and 90° C. and with increasing preference between 50° C. and 85° C., between 55° C. and 80° C., between 60° C. and 80° C., and most preferably between 65° C. and 75° C., for example at 65° C.

In this variant of the invention, step b) generally takes place over a period of 5 min to 12 h, preferably 15 min to 10 h and particularly preferably 30 min to 4 h.

The reaction is typically conducted at standard pressure, but can also be conducted at elevated or reduced pressure.

The desired compounds of the formula (II) can be isolated, for example, by aqueous workup in the presence of saturated ammonium chloride or sodium thiosulfate solutions and/or subsequent chromatography. Such methods are known to those skilled in the art and also include crystallization from an organic solvent or solvent mixture.

One example of a particularly preferred embodiment of the process according to the invention can be elucidated with reference to the following scheme (II):

Scheme II

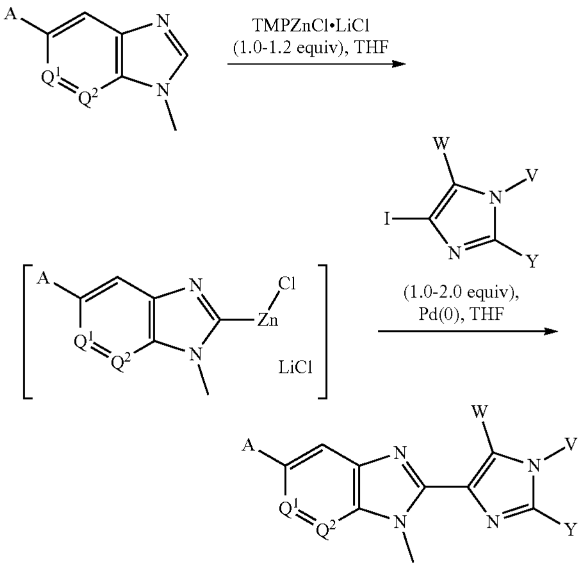

Here, A, $Q^1$, $Q^2$, V, W and Y have the definitions given above. The compound shown in brackets represents the corresponding intermediate of the formula (IIIa) which is converted further to the product, a compound of the formula (II). Both reactions take place in THF as solvent. "equiv" refers to the amount of equivalents of TMPZnCl.LiCl or compound of the formula (I) used. Pd(0) represents a palladium compound as catalyst, preferably $Pd(PPh_3)_4$.

The present invention is elucidated in more detail by the examples which follow, although the examples should not be interpreted in a manner that restricts the invention.

Analytical Determinations

The analytical determination methods described below apply to all statements in the entire document unless the respective analytical determination method is specially described in the relevant text passage.

Mass Spectrometry

The determination of $[M+H]^+$ or $M^-$ by LC-MS under acidic chromatographic conditions was carried out using 1 ml of formic acid per litre of acetonitrile and 0.9 ml of formic acid per litre of Millipore water as mobile phases. The Zorbax Eclipse Plus C18 50 mm*2.1 mm, 1.8 μm column was used at a column oven temperature of 55° C.

Instruments:

LC-MS3: Waters UPLC with SQD2 mass spectrometer and SampleManager sample changer. Linear gradient from 0.0 to 1.70 minutes from 10% acetonitrile to 95% acetonitrile, from 1.70 to 2.40 minutes constant 95% acetonitrile, flow rate 0.85 ml/min.

LC-MS6 and LC-MS7: Agilent 1290 LC, Agilent MSD mass spectrometer, HTS PAL sample changer. Linear gradient from 0.0 to 1.80 minutes from 10% acetonitrile to 95% acetonitrile, from 1.80 to 2.50 minutes constant 95% acetonitrile, flow rate 1.0 ml/min.

The determination of $[M+H]^+$ by LC-MS under neutral chromatographic conditions was carried out using acetonitrile and Millipore water with 79 mg/l ammonium carbonate as mobile phases.

Instruments:

LC-MS4: Waters IClass Acquity with QDA mass spectrometer and FTN sample changer (column Waters Acquity 1.7 μm 50 mm*2.1 mm, column oven temperature 45° C.). Linear gradient from 0.0 to 2.10 minutes from 10% acetonitrile to 95% acetonitrile, from 2.10 to 3.00 minutes constant 95% acetonitrile, flow rate 0.7 ml/min.

LC-MS5: Agilent 1100 LC system with MSD mass spectrometer and HTS PAL sample changer (column: Zorbax XDB C18 1.8 μm 50 mm*4.6 mm, column oven temperature 55° C.). Linear gradient from 0.0 to 4.25 minutes from 10% acetonitrile to 95% acetonitrile, from 4.25 to 5.80 minutes constant 95% acetonitrile, flow rate 2.0 ml/min.

In all cases, the retention time indices were determined from a calibration measurement of a homologous series of straight-chain alkan-2-ones having 3 to 16 carbons, where the index of the first alkanone was set to 300, the index of the last alkanone was set to 1600 and linear interpolation was carried out between the values of successive alkanones.

Log P Values

The log P values were determined according to EEC Directive 79/831 Annex V.A8 by HPLC (high-performance liquid chromatography) on a reversed-phase column (C18) using the following methods: The log P[a] value is determined by LC-UV measurement in the acidic range using 0.9 ml/l formic acid in water and 1.0 ml/l formic acid in acetonitrile as mobile phases (linear gradient from 10% acetonitrile to 95% acetonitrile).

The log P[n] value is determined by LC-UV measurement in the neutral range using 79 mg/l ammonium carbonate in water and acetonitrile as mobile phases (linear gradient from 10% acetonitrile to 95% acetonitrile).

Calibration was carried out using a homologous series of straight-chain alkan-2-ones (having 3 to 16 carbon atoms) with known log P values. The values between successive alkanones are determined by linear regression.

The $^1H$ NMR spectra were measured with a Bruker Avance III 400 MHz spectrometer fitted with a 1.7 mm TCI sample head using tetramethylsilane as standard (0.00 ppm), of solutions in the solvents $CD_3CN$, $CDCl_3$ or $d_6$-DMSO. Alternatively, a Bruker Avance III 600 MHz spectrometer fitted with a 5 mm CPNMP sample head or a Bruker Avance NEO 600 MHz spectrometer fitted with a 5 mm TCI sample head was employed for the measurements. In general, the measurements were carried out at a sample head temperature of 298 K. If other measurement temperatures were used, this is specifically mentioned.

The NMR data are stated in classic form (δ values, multiplet splitting, number of hydrogen atoms).

In each case, the solvent in which the NMR spectrum was recorded is stated.

EXAMPLE 1

Synthesis of 6-[5-(ethylsulfanyl)-1-methyl-1H-imidazol-4-yl]-7-methyl-3-(trifluoromethyl)-7H-imidazo[4,5-c]pyridazine

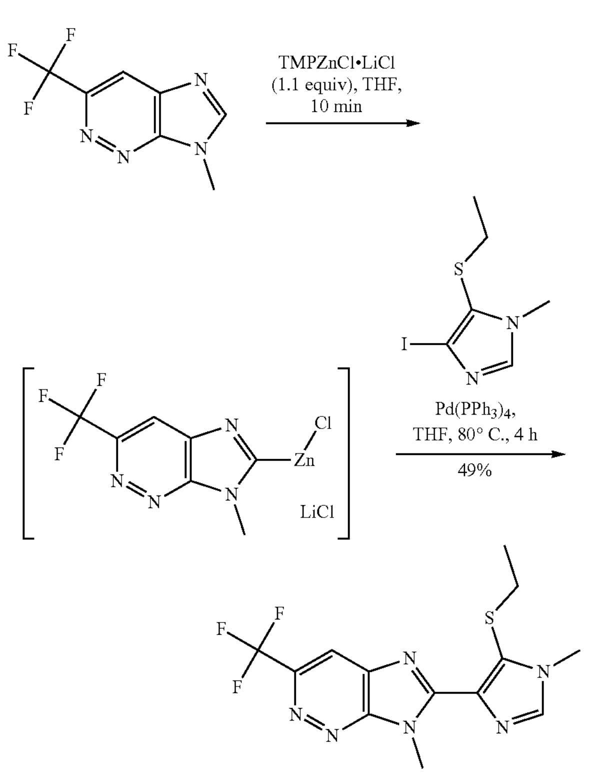

7-Methyl-3-(trifluoromethyl)-7H-imidazo[4,5-c]pyridazine (2.00 g, 9.91 mmol) in anhydrous THF (15 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31 M in THF, 8.33 ml, 10.9 mmol) was added dropwise and the mixture was stirred at 25° C. for 10 minutes. A solution of 5-(ethylsulfanyl)-4-iodo-1-methyl-1H-imidazole (2.66 g, 9.92 mmol) in anhydrous THF (22.5 ml) and tetrakis(triphenylphosphine)palladium(0) (1.15 g, 0.991 mmol) were added, and the reaction mixture was then stirred at 80° C. for 4 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 6-[5-(ethylsulfanyl)-1-methyl-1H-imidazol-4-yl]-7-methyl-3-(trifluoromethyl)-7H-imidazo[4,5-c]pyridazine (1.65 g, 49%) as a white solid.

HPLC-MS: log P[a]=2.26; log P[n]=2.37; $MH^+$: 343;

$^1$H-NMR ($d_6$-DMSO): δ 8.52 (s, 1H), 8.23 (s, 1H), 4.32 (s, 3H), 3.80 (s, 3H), 3.06 (q, 2H), 1.11 (t, 3H).

EXAMPLE 2

Synthesis of 6-[2-(4-chlorophenyl)-5-(ethylsulfanyl)-1-methyl-1H-imidazol-4-yl]-7-methyl-3-(trifluoromethyl)-7H-imidazo[4,5-c]pyridazine

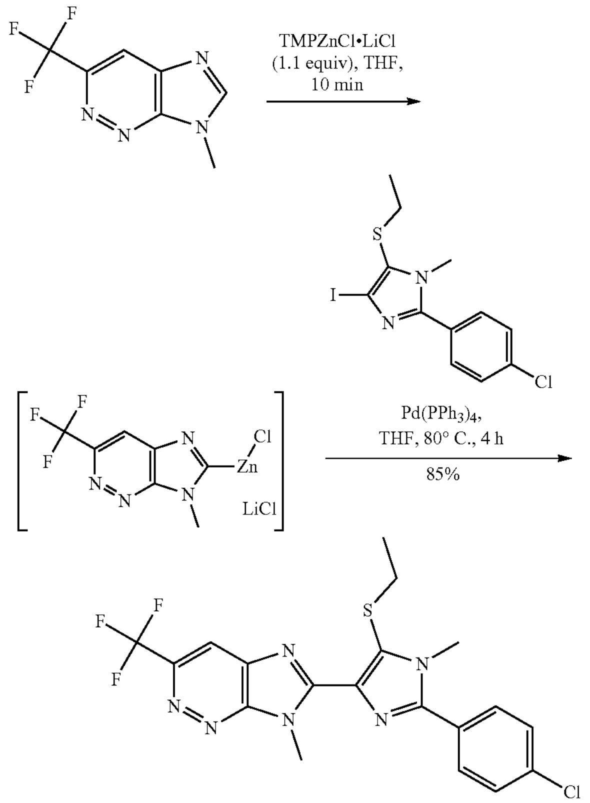

7-Methyl-3-(trifluoromethyl)-7H-imidazo[4,5-c]pyridazine (220 mg, 1.09 mmol) in anhydrous THF (1.5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31 M in THF, 0.914 ml, 1.09 mmol) was added dropwise and the mixture was stirred at 25° C. for 10 minutes. A solution of 2-(4-chlorophenyl)-5-(ethylsulfanyl)-4-iodo-1-methyl-1H-imidazole (412 mg, 1.20 mmol) in anhydrous THF (2.5 ml) and tetrakis(triphenylphosphine)palladium(0) (49.3 mg, 0.109 mmol) were added, and the reaction mixture was then stirred at 80° C. for 4 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 6-[2-(4-chlorophenyl)-5-(ethylsulfanyl)-1-methyl-1H-imidazol-4-yl]-7-methyl-3-(trifluoromethyl)-7H-imidazo[4,5-c]pyridazine (420 mg, 85%) as a white solid.

HPLC-MS: log P[a]=4.23; log P[n]=4.08; $MH^+$: 453;

$^1$H-NMR ($d_6$-DMSO): δ 8.57 (s, 1H), 7.91 (d, 2H), 7.66 (d, 2H), 4.37 (s, 3H), 3.90 (s, 3H), 3.09 (q, 2H), 1.18 (t, 3H).

COMPARATIVE EXAMPLE

Synthesis of 6-[2-(4-chlorophenyl)-5-(ethylsulfanyl)-1-methyl-1H-imidazol-4-yl]-7-methyl-3-(trifluoromethyl)-7H-imidazo[4,5-c]pyridazine According to the Prior Art (WO 2018/130443)

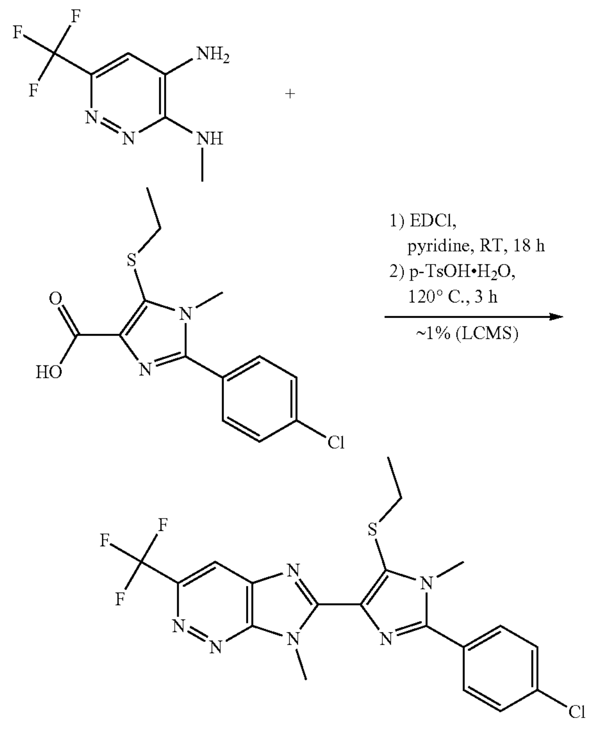

$N^3$-Methyl-6-(trifluoromethyl)pyridazine-3,4-diamine (200 mg, 1.04 mmol) and 1-(3-dimethylaminopropyl)-3-ethylcarbodiimide hydrochloride (EDCI, 200 mg, 1.04 mmol) were added to a solution of 2-(4-chlorophenyl)-5-(ethylsulfanyl)-1-methyl-1H-imidazole-4-carboxylic acid (402 mg, 1.35 mmol) in pyridine (16.1 ml). The mixture was stirred at 25° C. overnight. p-Toluenesulfonic acid (179 mg, 1.04 mmol) was added and the mixture was stirred at 120° C. for 3 h. Subsequently, the reaction mixture was cooled to room temperature. The mixture was freed of the solvent under reduced pressure. According to HPLC-MS, the crude product contains about 1% 6-[2-(4-chlorophenyl)-5-(ethylsulfanyl)-1-methyl-1H-imidazol-4-yl]-7-methyl-3-(trifluoromethyl)-7H-imidazo[4,5-c]pyridazine.

HPLC-MS: log P[a]=4.35; log P[n]=4.07; $MH^+$: 453;

The following compounds, listed in Table 2, were prepared analogously to 6-[2-(4-chlorophenyl)-5-(ethylsulfanyl)-1-methyl-1H-imidazol-4-yl]-7-methyl-3-(trifluoromethyl)-7H-imidazo[4,5-c]pyridazine.

TABLE 2

| Structure | Analysis |
|---|---|
| 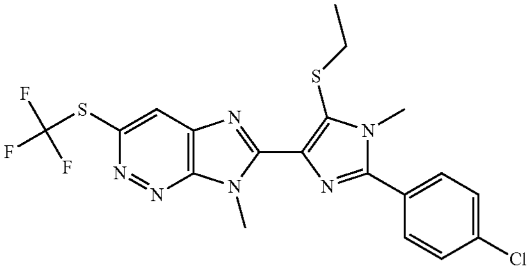 [SMILES: CCSc1c(-c2nc3cc(SC(F)(F)F)nnc3n2C)nc(-c2ccc(Cl)cc2)n1C] | HPLC-MS: logP[a] = 4.51; logP[n] = 4.34; $MH^+$: 485; $^1$H-NMR ($d_6$-DMSO): δ 8.48 (s, 1H), 7.90 (d, 2H), 7.66 (d, 2H), 4.33 (s, 3H), 3.89 (s, 3H), 3.09 (q, 2H), 1.18 (t, 3H). |
| 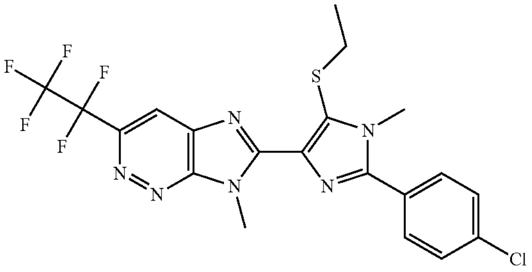 [SMILES: CCSc1c(-c2nc3cc(C(F)(F)C(F)(F)F)nnc3n2C)nc(-c2ccc(Cl)cc2)n1C] | HPLC-MS: logP[a] = 4.82; logP[n] = 4.60; $MH^+$: 503; $^1$H-NMR ($d_6$-DMSO): δ 8.59 (s, 1H), 7.91 (d, 2H), 7.66 (d, 2H), 4.37 (s, 3H), 3.90 (s, 3H), 3.10 (q, 2H), 1.18 (t, 3H). |
| 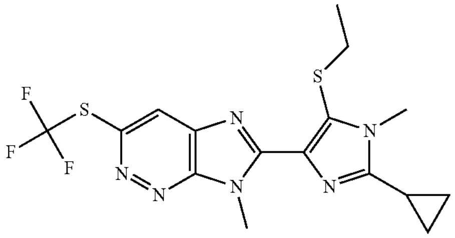 [SMILES: CCSc1c(-c2nc3cc(SC(F)(F)F)nnc3n2C)nc(C2CC2)n1C] | HPLC-MS: logP[a] = 3.50; logP[n] = 3.40; $MH^+$: 415; $^1$H-NMR ($d_6$-DMSO): δ 8.405 (s, 1H), 4.24 (s, 3H), 3.82 (s, 3H), 3.00 (q, 2H), 2.20 (m, 1H), 1.11 (t, 3H), 1.05 (m, 2H), 1.01 (m, 2H). |
| 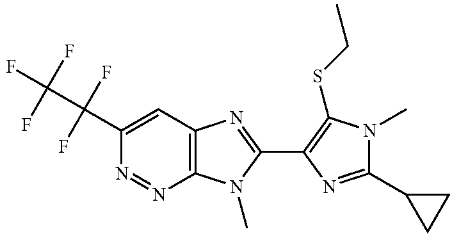 [SMILES: CCSc1c(-c2nc3cc(C(F)(F)C(F)(F)F)nnc3n2C)nc(C2CC2)n1C] | HPLC-MS: logP[a] = 3.85; logP[n] = 3.75; $MH^+$: 433; $^1$H-NMR ($d_6$-DMSO): δ 8.51 (s, 1H), 4.28 (s, 3H), 3.83 (s, 3H), 3.02 (q, 2H), 2.21 (m, 1H), 1.12 (t, 3H), 1.05 (m, 2H), 1.01 (m, 2H). |
| 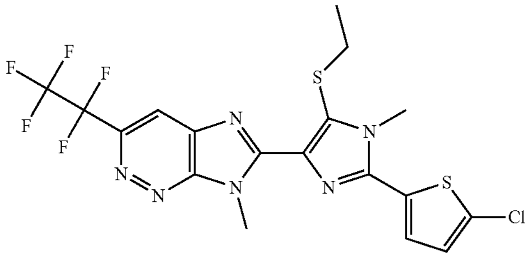 [SMILES: CCSc1c(-c2nc3cc(C(F)(F)C(F)(F)F)nnc3n2C)nc(-c2ccc(Cl)s2)n1C] | HPLC-MS: logP[a] = 5.14; logP[n] = 4.92; $MH^+$: 509; $^1$H-NMR ($d_6$-DMSO): δ 8.59 (s, 1H), 7.62 (d, 1H), 7.31 (d, 1H), 4.35 (s, 3H), 4.01 (s, 3H), 3.07 (q, 2H), 1.16 (t, 3H). |

TABLE 2-continued

| Structure | Analysis |
| --- | --- |
| 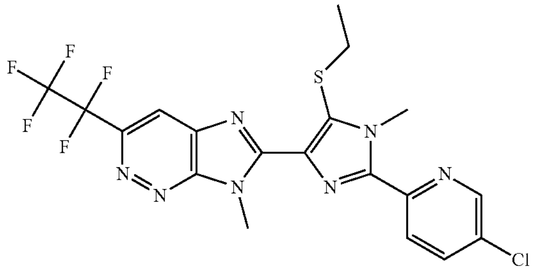 [SMILES: CCSc1c(-c2nc3cc(C(F)(F)C(F)(F)F)nnc3n2C)nc(-c2ccc(Cl)cn2)n1C] | HPLC-MS: logP[a] = 5.25; logP[n] = 4.66; $MH^+$: 504; $^1H$-NMR ($d_6$-DMSO): δ 8.80 (m, 1H), 8.60 (s, 1H), 8.30 (d, 1H), 8.16 (m, 1H), 4.41 (s, 3H), 4.22 (s, 3H), 3.115 (q, 2H), 1.16 (t, 3H). |

EXAMPLE 3

Synthesis of 6-[5-(ethylsulfanyl)-1-methyl-1H-imidazol-4-yl]-7-methyl-3-(pentafluoroethyl)-7H-imidazo[4,5-c]pyridazine

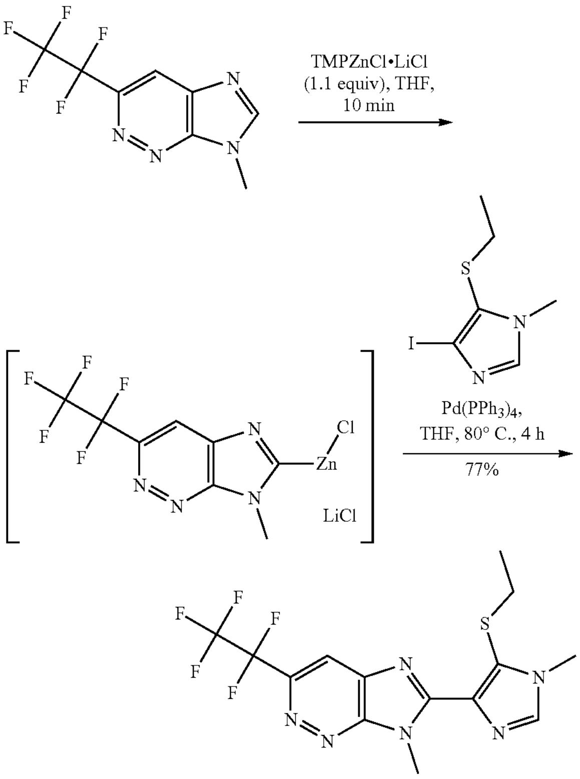

7-Methyl-3-(pentafluoroethyl)-7H-imidazo[4,5-c] pyridazine (5.00 g, 19.8 mmol) in anhydrous THF (30 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31 M in THF, 16.7 ml, 21.8 mmol) was added dropwise and the mixture was stirred at 25° C. for 10 minutes. A solution of 5-(ethylsulfanyl)-4-iodo-1-methyl-1H-imidazole (5.32 g, 19.8 mmol) in anhydrous THF (45 ml) and tetrakis(triphenylphosphine)palladium(0) (2.29 g, 1.98 mmol) were added, and the reaction mixture was then stirred at 80° C. for 4 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 6-[5-(ethylsulfanyl)-1-methyl-1H-imidazol-4-yl]-7-methyl-3-(pentafluoroethyl)-7H-imidazo [4,5-c]pyridazine (6.10 g, 77%) as a white solid.

HPLC-MS: log P[a]=2.88; log P[n]=2.86; $MH^+$: 393; $^1H$-NMR ($d_6$-DMSO): δ 8.55 (s, 1H), 8.235 (s, 1H), 4.33 (s, 3H), 3.80 (s, 3H), 3.07 (q, 2H), 1.115 (t, 3H).

EXAMPLE 4

Synthesis of 6-[5-(ethylsulfonyl)-1-methyl-1H-imidazol-4-yl]-7-methyl-3-(pentafluoroethyl)-7H-imidazo[4,5-c]pyridazine

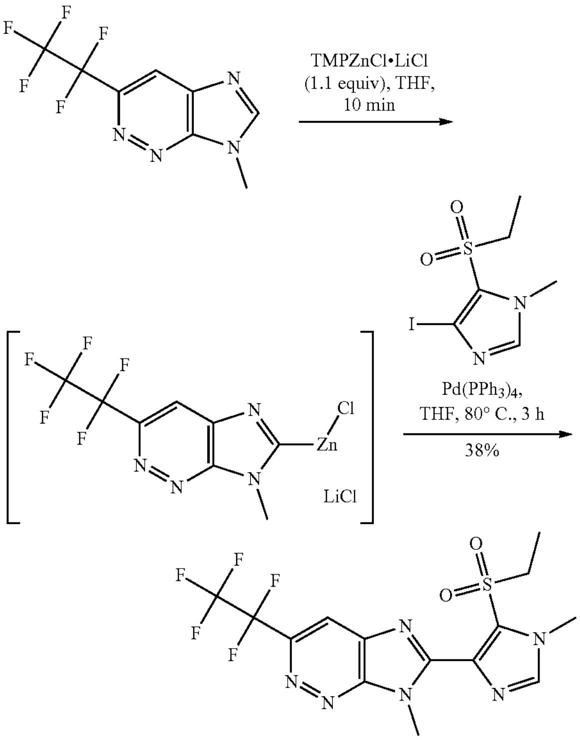

7-Methyl-3-(pentafluoroethyl)-7H-imidazo[4,5-c]pyridazine (100 mg, 0.397 mmol) in anhydrous THF (1.5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31 M in THF, 0.333 ml, 0.436 mmol) was added dropwise and the mixture was stirred at 25° C. for 10 minutes. A solution of 5-(ethylsulfonyl)-4-iodo-1-methyl-1H-imidazole (119 mg, 0.397 mmol) in anhydrous THF (2.5 ml) and tetrakis(triphenylphosphine) palladium(0) (45.8 mg, 0.040 mmol) were added, and the reaction mixture was then stirred at 80° C. for 3 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 6-[5-(ethylsulfonyl)-1-methyl-1H-imidazol-4-yl]-7-methyl-3-(pentafluoroethyl)-7H-imidazo[4,5-c]pyridazine (68.2 mg, 38%) as a white solid.

HPLC-MS: log P[a]=2.20; log P[n]=2.21; $MH^+$: 425;

$^1$H-NMR ($d_6$-DMSO): δ 8.71 (s, 1H), 8.37 (s, 1H), 4.12 (s, 3H), 3.99 (s, 3H), 3.85 (q, 2H), 1.285 (t, 3H).

EXAMPLE 5

Synthesis of 6-[2-bromo-5-(ethylsulfanyl)-1-methyl-1H-imidazol-4-yl]-7-methyl-3-(pentafluoroethyl)-7H-imidazo[4,5-c]pyridazine

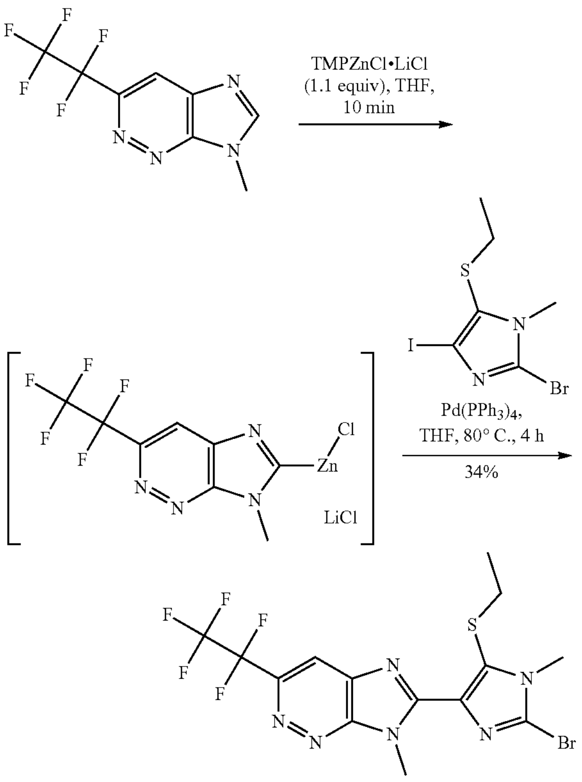

7-Methyl-3-(pentafluoroethyl)-7H-imidazo[4,5-c]pyridazine (50.0 mg, 0.198 mmol) in anhydrous THF (5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31 M in THF, 0.167 ml, 0.218 mmol) was added dropwise and the mixture was stirred at 25° C. for 10 minutes. A solution of 2-bromo-5-(ethylsulfanyl)-4-iodo-1-methyl-1H-imidazole (68.8 mg, 0.198 mmol) in anhydrous THF (10 ml) and tetrakis(triphenylphosphine)palladium(0) (22.9 mg, 0.020 mmol) were added, and the reaction mixture was then stirred at 80° C. for 4 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 6-[2-bromo-5-(ethylsulfanyl)-1-methyl-1H-imidazol-4-yl]-7-methyl-3-(pentafluoroethyl)-7H-imidazo[4,5-c]pyridazine (35.8 mg, 34%) as a white solid.

HPLC-MS: log P[a]=3.76; log P[n]=3.66; $MH^+$: 471;

$^1$H-NMR ($d_6$-DMSO): δ 8.59 (s, 1H), 4.28 (s, 3H), 3.78 (s, 3H), 3.06 (q, 2H), 1.13 (t, 3H).

EXAMPLE 6

Synthesis of 2-[5-(ethylsulfanyl)-1-methyl-1H-imidazol-4-yl]-3-methyl-6-(pentafluoroethyl)-3H-imidazo[4,5-c]pyridine

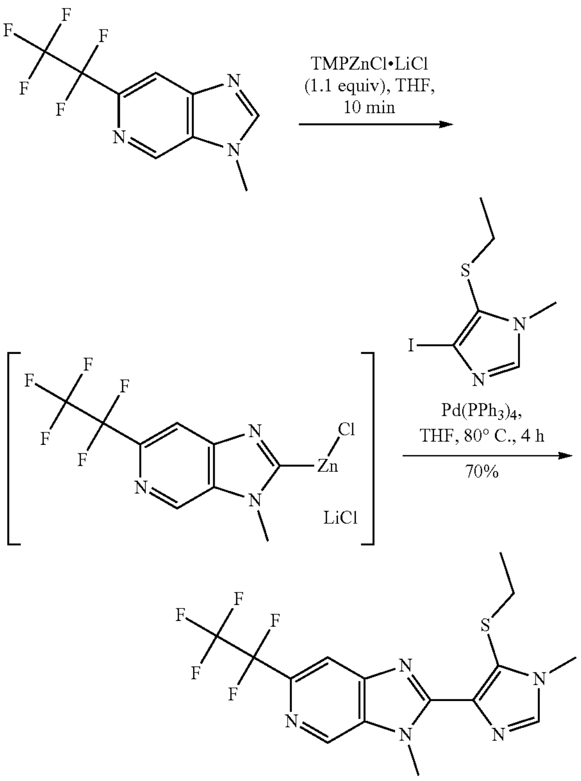

3-Methyl-6-(pentafluoroethyl)-3H-imidazo[4,5-c]pyridazine (160 mg, 0.637 mmol) in anhydrous THF (5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31 M in THF, 0.535 ml, 0.701 mmol) was added dropwise and the mixture was stirred at 25° C. for 10 minutes. A solution of 5-(ethylsulfanyl)-4-iodo-1-methyl-1H-imidazole (171 mg, 0.637 mmol) in anhydrous THF (10 ml) and tetrakis(triphenylphosphine) palladium(0) (73.6 mg, 0.064 mmol) were added, and the reaction mixture was then stirred at 80° C. for 4 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 2-[5-(ethylsulfanyl)-1-methyl-1H-imidazol-4-yl]-3-methyl-6-(pentafluoroethyl)-3H-imidazo[4,5-c]pyridine (174 mg, 70%) as a white solid.

HPLC-MS: log P[a]=2.70; log P[n]=2.71; $MH^+$: 392;

$^1$H-NMR ($d_6$-DMSO): δ 9.15 (s, 1H), 8.18 (s, 1H), 8.16 (s, 1H), 4.20 (s, 3H), 3.78 (s, 3H), 3.02 (q, 2H), 1.09 (t, 3H).

EXAMPLE 7

Synthesis of 6-bromo-2-[2-cyclopropyl-5-(ethylsulfanyl)-1-methyl-1H-imidazol-4-yl]-3-methyl-3H-imidazo[4,5-b]pyridine

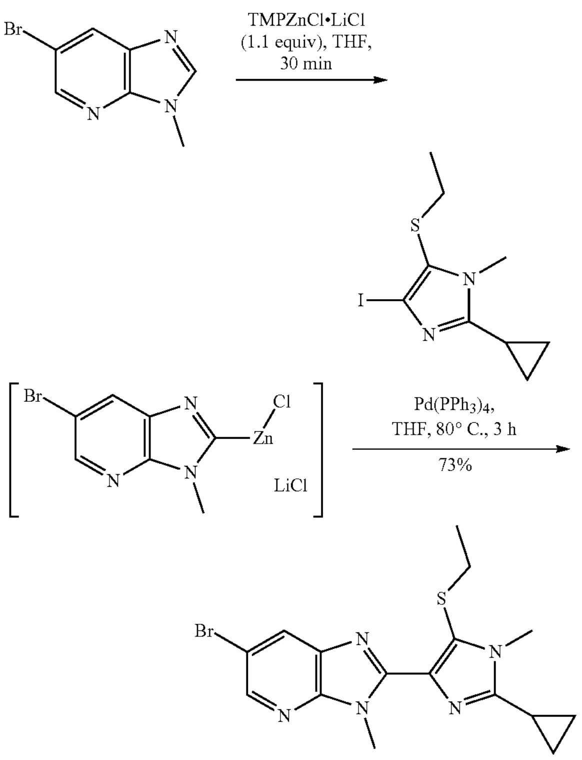

6-Bromo-3-methyl-3H-imidazo[4,5-b]pyridine (250 mg, 1.18 mmol) in anhydrous THF (5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl-.LiCl) (1.31 M in THF, 0.990 ml, 1.30 mmol) was added dropwise and the mixture was stirred at 25° C. for 30 minutes. A solution of 2-cyclopropyl-5-(ethylsulfanyl)-4-iodo-1-methyl-1H-imidazole (436 mg, 1.41 mmol) in anhydrous THF (10 ml) and tetrakis(triphenylphosphine)palladium(0) (136 mg, 0.118 mmol) were added, and the reaction mixture was then stirred at 80° C. for 3 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 6-bromo-2-[2-cyclopropyl-5-(ethylsulfanyl)-1-methyl-1H-imidazol-4-yl]-3-methyl-3H-imidazo[4,5-b]pyridine (350 mg, 73%) as a white solid.

HPLC-MS: log P[a]=2.92; log P[n]=3.23; $MH^+$: 392;

$^1$H-NMR ($d_6$-DMSO): δ 8.42 (d, 1H), 8.32 (d, 1H), 3.97 (s, 3H), 3.79 (s, 3H), 2.94 (q, 2H), 2.16 (m, 1H), 1.08 (t, 3H), 1.02 (m, 2H), 0.97 (m, 2H).

EXAMPLE 8

Synthesis of 2-[2-bromo-5-(ethylsulfanyl)-1-methyl-1H-imidazol-4-yl]-3-methyl-6-(trifluoromethyl)-3H-imidazo[4,5-c]pyridine Step 1

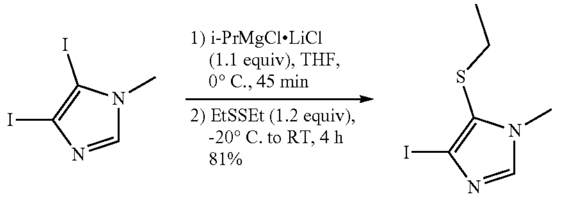

4,5-Diiodo-1-methyl-1H-imidazole (5.00 g, 15.0 mmol) in anhydrous THF (35 ml) was initially charged in a dry, argon-filled Schlenk flask, equipped with a magnetic stirrer bar and a septum. Isopropylmagnesium chloride lithium chloride complex (i-PrMgCl.LiCl) (1.3 M in THF, 12.7 ml, 16.5 mmol) was added dropwise at 0° C. and the mixture was stirred at 0° C. for 45 minutes. Diethyl disulfide (2.21 ml, 18.0 mmol) was added dropwise at −20° C. and the reaction mixture was then stirred at room temperature for 4 hours. Saturated aqueous ammonium chloride solution was added to the reaction mixture which was extracted with dichloromethane, and the extract was dried over anhydrous sodium sulfate. Following filtration, the solvent was removed under reduced pressure. The crude product was purified by chromatography, which gave 5-(ethylsulfanyl)-4-iodo-1-methyl-1H-imidazole (2.60 g, 81%) as a colourless oil.

HPLC-MS: log P[a]=1.61; log P[n]=1.91; $MH^+$: 269;

$^1$H-NMR ($d_6$-DMSO): δ 7.88 (s, 1H), 3.69 (s, 3H), 2.68 (q, 2H), 1.10 (t, 3H).

Step 2

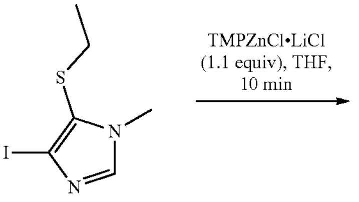

-continued

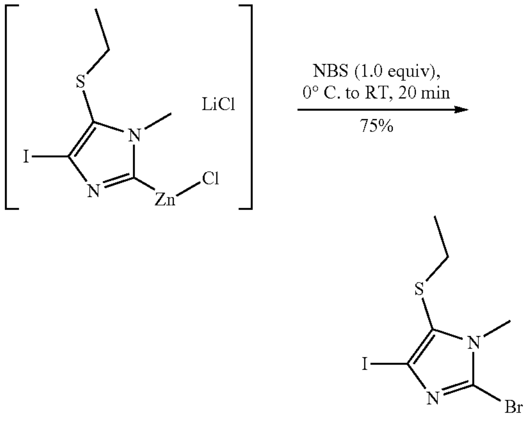

5-(Ethylsulfanyl)-4-iodo-1-methyl-1H-imidazole (336 mg, 1.25 mmol) in anhydrous THF (5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.3 M in THF, 1.06 ml, 1.38 mmol) was added dropwise and the mixture was stirred at 25° C. for 10 minutes. A solution of N-bromosuccinimide (223 mg, 1.25 mmol) in anhydrous THF (7.4 ml) was added dropwise at 0° C., and the reaction mixture was then stirred at room temperature for 20 minutes. Saturated aqueous ammonium chloride solution and sodium thiosulfate solution were added to the reaction mixture which was extracted three times with ethyl acetate, and the extract was dried over anhydrous sodium sulfate. Following filtration, the solvent was removed under reduced pressure. The crude product was purified by chromatography, which gave 2-bromo-5-(ethylsulfanyl)-4-iodo-1-methyl-1H-imidazole (328 mg, 75%) as a white solid.

HPLC-MS: log P[a]=2.77; log P[n]=2.68; $MH^+$: 347;

$^1$H-NMR ($d_6$-DMSO): δ 3.66 (s, 3H), 2.70 (q, 2H), 1.12 (t, 3H).

Step 3

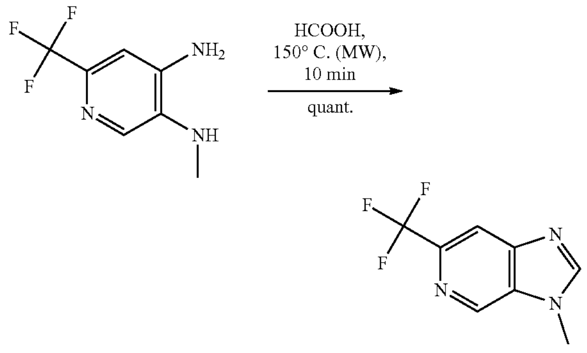

A solution of $N^3$-methyl-6-(trifluoromethyl)pyridine-3,4-diamine (1.50 g, 7.85 mmol) in formic acid (4 ml) was stirred in a microwave oven at 150° C. for one hour. The reaction mixture was cooled to 25° C. and the solvent was removed under reduced pressure. The crude product was purified by chromatography, which gave 3-methyl-6-(trifluoromethyl)-3H-imidazo[4,5-c]pyridine (1.80 g, quant.) as a white solid.

HPLC-MS: log P[a]=1.04; log P[n]=1.10; $MH^+$: 202;

$^1$H-NMR ($d_6$-DMSO): δ 9.14 (s, 1H), 8.61 (s, 1H), 8.18 (s, 1H), 4.02 (s, 3H).

Step 4

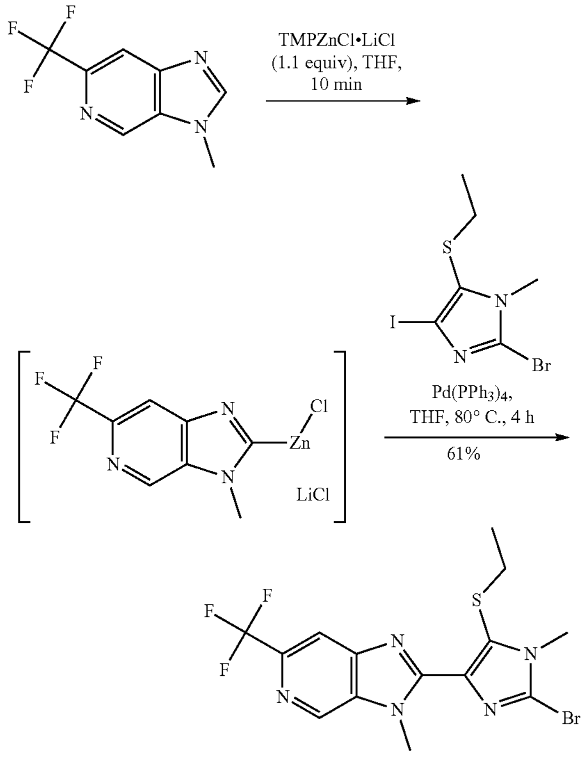

3-Methyl-6-(trifluoromethyl)-3H-imidazo[4,5-c] pyridazine (200 mg, 0.994 mmol) in anhydrous THF (4 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.18 M in THF, 0.927 ml, 1.09 mmol) was added dropwise and the mixture was stirred at 25° C. for 10 minutes. A solution of 2-bromo-5-(ethylsulfanyl)-4-iodo-1-methyl-1H-imidazole (345 mg, 0.994 mmol) in anhydrous THF (9 ml) and tetrakis(triphenylphosphine)palladium(0) (115 mg, 0.099 mmol) were added, and the reaction mixture was then stirred at 80° C. for 4 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 2-[2-bromo-5-(ethylsulfanyl)-1-methyl-1H-imidazol-4-yl]-3-methyl-6-(trifluoromethyl)-3H-imidazo[4,5-c]pyridine (274 mg, 61%) as a white solid.

HPLC-MS: log P[a]=3.04; log P[n]=2.85; $MH^+$: 420;

$^1$H-NMR ($d_6$-DMSO): δ 9.15 (s, 1H), 8.18 (s, 1H), 4.15 (s, 3H), 3.76 (s, 3H), 3.00 (q, 2H), 1.11 (t, 3H).

This method allows the preparation of 2-[2-bromo-5-(ethylsulfanyl)-1-methyl-1H-imidazol-4-yl]-3-methyl-6-(trifluoromethyl)-3H-imidazo[4,5-c]pyridine from 4,5-diiodo-1-methyl-1H-imidazole in 4 steps in a total yield of 37%.

COMPARATIVE EXAMPLE

The route from the prior art (WO 2018/130443) allows the preparation of 2-[2-bromo-5-(ethylsulfanyl)-1-methyl-1H-imidazol-4-yl]-3-methyl-6-(trifluoromethyl)-3H-imidazo[4,5-c]pyridine from ethyl 1-methyl-1H-imidazole-4-carboxylate in 4 steps in a total yield of 21%.

where $R^7$ represents methyl, ethyl, n-propyl or isopropyl, and

A represents bromine, trifluoromethyl, pentafluoroethyl or trifluoromethylthio,

W represents $S(O)nR^8$, where $R^8$ represents ethyl and n represents 0 or 2,

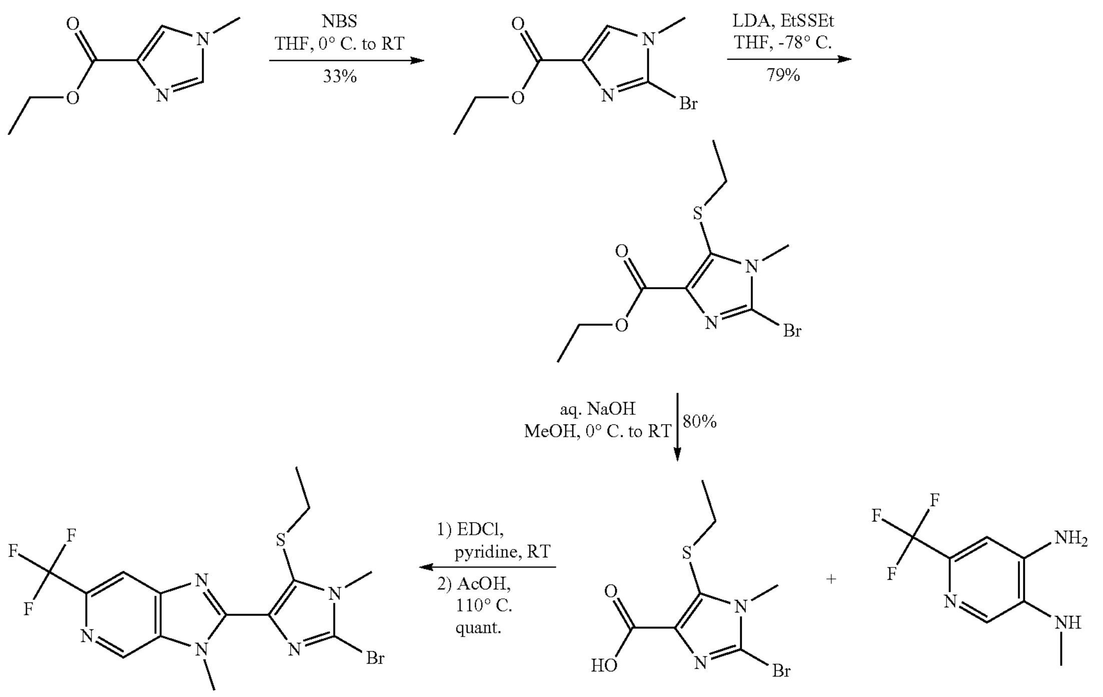

The invention claimed is:

1. A process for preparing a compound of formula (II)

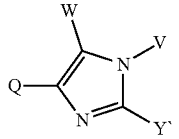

wherein

Q represents a structural element Q2, Q3, or Q13,

Q2

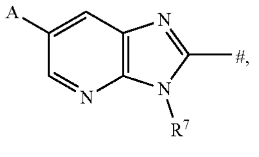

Q3

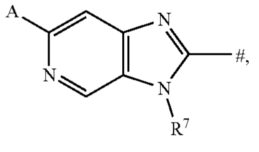

Q13

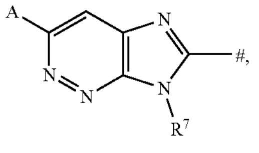

V represents methyl and

Y represents hydrogen, bromine, cyclopropyl, para-chlorophenyl, cyanocyclopropyl-phenyl, 5-chlorothien-2-yl or 5-chloro-2-pyridine, wherein, in a first process step a), a compound Q-H in which Q is as defined above is reacted with an organozinc base of formula (V)

(V) (TMP) ZnCI to give a compound of formula (IIIa) or formula (IIIb)

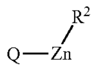

(IIIa)

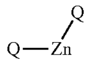

(IIIb), wherein Q has the definition given above and $R^2$ is chlorine, and, in a second process step b), reacting the compound of formula (IIIa) or (IIIb) with a compound of formula (I)

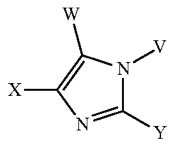

wherein X represents iodine and V, W and Y each have the meanings mentioned above, in the presence of a catalyst, to give the compound of the formula (II).

2. The process according to Claim 1, wherein Q represents Q3.

3. The process according to Claim 1, wherein Q represents Q13.

4. The process according to claim 1, wherein the organozinc base is present in conjunction with an alkali metal halide or alkaline earth metal halide, optionally lithium chloride or magnesium chloride.

5. The process according to claim 1, wherein the organozinc base is used in a total amount of 0.5 to 5.0 equivalents, based on the compound Q-H.

6. The process according to claim 1, wherein the compound of formula (I) is used in a total amount of 0.5 to 10 equivalents, based on the compound Q-H.

7. The process according to claim 1, wherein the catalyst is a palladium compound.

8. The process according to claim 1, wherein the catalyst is tetrakis (triphenylphosphine) palladium (O).

9. The process according to Claim 1, carried out in the presence of a solvent, wherein the solvent is THF or N,N-dimethylformamide (DMF).

10. The process according to claim 1, wherein a) is carried out at a temperature between 0° C. and 80° C.

11. The process according to claim 1, wherein b) is carried out at a temperature between 40°° C. and 90° C.

12. The process according to claim 1, wherein $R^7$ is methyl.

* * * * *